United States Patent
Yoder et al.

(10) Patent No.: US 10,828,337 B2
(45) Date of Patent: Nov. 10, 2020

(54) MATERIALS AND METHODS FOR CONTROLLING VASCULOGENESIS FROM ENDOTHELIAL COLONY FORMING CELLS

(71) Applicant: Indiana University Research and Technology Corporation, Indianapolis, IN (US)

(72) Inventors: Mervin C. Yoder, Indianapolis, IN (US); Paul Critser, Indianapolis, IN (US); Sherry Voytik-Harbin, Zionsville, IN (US)

(73) Assignee: Indiana University Research and Technology Corporation, Indianapolis, IN (US)

( * ) Notice: Subject to any disclaimer, the term of this patent is extended or adjusted under 35 U.S.C. 154(b) by 28 days.

(21) Appl. No.: 15/891,252

(22) Filed: Feb. 7, 2018

(65) Prior Publication Data

US 2019/0000891 A1 Jan. 3, 2019

Related U.S. Application Data

(63) Continuation of application No. 14/123,483, filed as application No. PCT/US2012/040737 on Jun. 4, 2012, now abandoned.

(60) Provisional application No. 61/492,755, filed on Jun. 2, 2011.

(51) Int. Cl.
| | |
|---|---|
| *A61K 35/51* | (2015.01) |
| *A61K 9/70* | (2006.01) |
| *A61L 27/24* | (2006.01) |
| *A61L 27/38* | (2006.01) |

(52) U.S. Cl.
CPC .............. *A61K 35/51* (2013.01); *A61K 9/70* (2013.01); *A61L 27/24* (2013.01); *A61L 27/3808* (2013.01)

(58) Field of Classification Search
None
See application file for complete search history.

(56) References Cited

U.S. PATENT DOCUMENTS

| | | | |
|---|---|---|---|
| 7,771,717 B2 | 8/2010 | Badylak et al. | |
| 2008/0025956 A1 | 1/2008 | Yoder et al. | |
| 2008/0268052 A1 | 10/2008 | Voytik-Harbin et al. | |
| 2010/0143476 A1 | 6/2010 | March et al. | |

FOREIGN PATENT DOCUMENTS

WO 2010123928 A1 10/2010

OTHER PUBLICATIONS https://www.sigmaaldrich.com/content/dam/sigma-aldrich/docs/Sigma/Datasheet/3/c3867dat.pdf, Product Information, Collagen, Type I solution from rat tail, by Sigma-Aldrich, no journal, published online, 2 pages printed, printed Sep. 14, 2019, no Author provided.*
Wittington, et al. (2013) "Collagen-Polymer Guidance of Vessel Network Formation and Stabilization by Endothelial Colony Forming Cells in Vitro", Macromolecular Bioscience, 13: 1135-49.*
Yoder, et al. (2007) "Redefining endothelial progenitor cells via clonal analysis and hematopoietic stem/progenitor cell principals", Blood, 109(5): 1801-09.
Sweeney, et al. (1998) "Defining the domains of type I collagen involved in heparin-binding and endothelial tube formation", Proceedings of the National Academy of Science, USA, 95: 7275-80.
Bailey, J.L. et al., "Collagen Oligomers Modulate Physical and Biological Properties of Three-Dimensional Self-Assembled Matrices", Biopolymers, Aug. 24, 2010, pp. 77-93, vol. 95, No. 2.
International Search Report for PCT/US2012/040737, dated Dec. 10, 2012, pp. 1-3, issued by the Korean Intellectual Property Office.

* cited by examiner

*Primary Examiner* — Robert M Kelly
(74) *Attorney, Agent, or Firm* — Faegre Drinker Biddle & Reath LLP

(57) ABSTRACT

Materials and methods are disclosed for controlling vasculogenesis using building blocks of a collagen matrix and endothelial colony forming cells (ECFC). The building blocks may be isolated by fractionating an acid soluble Type I collagen. The building blocks comprising monomers and/or oligomers may be recombined in desired ratios to alter the matrix microenvironment and to influence ECFC behavior.

14 Claims, 30 Drawing Sheets

Specification includes a Sequence Listing.

MATERIALS AND METHODS FOR CONTROLLING VASCULOGENESIS FROM ENDOTHELIAL COLONY FORMING CELLS

PRIORITY CLAIM

This application is a continuation of U.S. patent application Ser. No. 14/123,483, filed Dec. 2, 2013, now abandoned, which is a U.S. National Phase filing of PCT/US2012/040737, filed Jun. 4, 2012, which claims the benefit of U.S. Provisional Patent Application No. 61/492,755, filed Jun. 2, 2011, the entire disclosures of all of which are hereby expressly incorporated by reference herein.

FIELD OF THE INVENTION

This invention relates generally to materials and methods for controlling vasculogenesis using for example some building blocks of collagen matrix, various cellular growth factors and endothelial colony forming cells (ECFC).

BACKGROUND

Impaired vascular perfusion is a contributor to many disease states, including peripheral and cardiovascular disease, failure of tissue and organ transplants, and impaired wound healing. The development of a functional vascular network is necessary for development of clinical scale tissue replacements to treat these disease states. Due to disease, defect and injury there is a need to promote the growth of new vasculature both in vivo and in vitro. When tissue is being developed, either in vivo or in vitro, for the treatment of a patient, there are a variety of circumstances under which it would be very useful to be able to control the size, shape, bio-mechanical and biological properties of the tissue being developed. Development of a functional vascular network is a major problem limiting current tissue engineering strategies targeting repair and regeneration of damaged or diseased tissue. Recently endothelial colony forming cells (ECFCs) have been shown to vascularize a Type I collagen scaffold in vivo. ECFCs are the only cells that have been shown to possess direct in vivo vessel forming ability upon transplantation. This has generated much interest in the use of ECFCs for tissue engineering strategies. However, there is still a great need for refinement of a defined microenvironment to locally deliver ECFCs and guide vessel formation in vivo. Some aspects of the invention disclosed herein address this need.

SEQUENCE LISTING

SEQ ID. NO. 1 CCACTACCAAGAAGGGATCTATCA; forward primer for ATP5B.

SEQ ID. NO. 2 GGGCAGGGTCAGTCAAGTC; reverse primer for ATP5B.

SEQ ID. NO. 3 CATCGGAATATGTACCGACTGTT primer for Cdc42.

SEQ ID. NO. 4 TGCAGTATCAAAAAGTCCAAGAGTA reverse primer for Cdc42.

SEQ ID. NO. 5 CTGTCAGGAATGAGGATCTGAA primer for MT1-MMP.

SEQ ID. NO. 6 AGGGGTCACTGGAATGCTC reverse primer for MT1-MMP.

SEQUENCE LISTING -continued

SEQ ID. NO. 7 CTGATCAGTTACACAACCAATGC primer for Rac1.

SEQ ID. NO. 8 CATTGGCAGAATAATTGTCAAAGA reverse primer for Rac1.

DEFINITIONS

Figure 1:
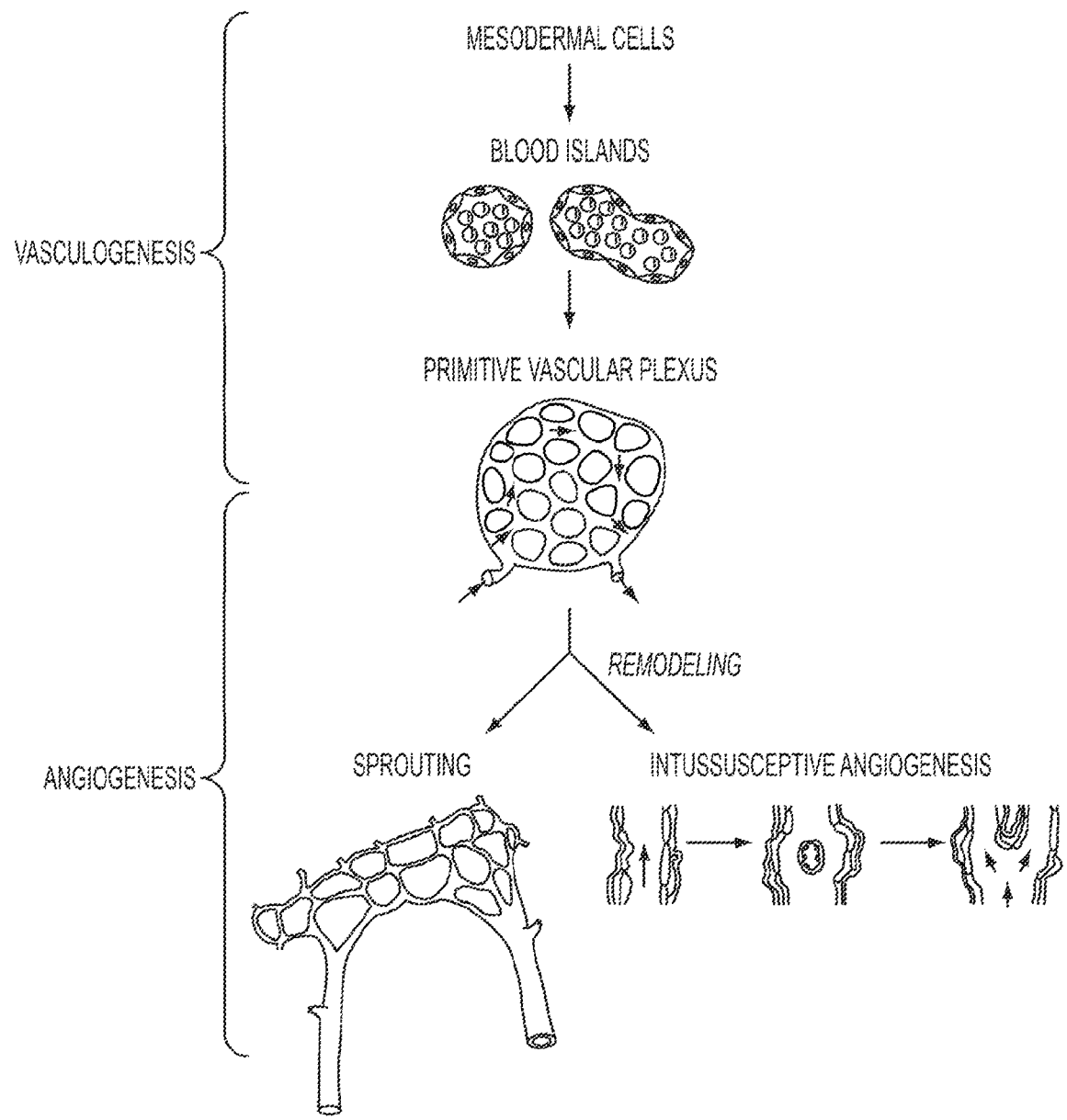
FIG. 1. Cartoon illustrating some steps in development blood vessel formation and some elements of the vascular system.

The following terms are defined as used herein, unless explicitly stated otherwise or clearly implied otherwise:

Collagen "monomers" represent single collagen molecules.

With respect to an acid soluble Type I collagen, a "monomer-rich fraction" of the collagen is quantified as having an average molecular weight (AMW) of about 282 kDA.

Collagen "oligomers" represent covalently cross-linked monomers (e.g., dimers=2 monomers, trimers=3 monomers, etc.).

Unless noted otherwise as used herein the acronym PSC refers to Pig Skin Collagen.

With respect to an acid soluble Type I collagen, an "oligomer-rich fraction" of the collagen is quantified as having an AMW of about 603 kDA.

The term "about" refers to a range of values plus or minus 10 percent (e.g. about 1.0 encompasses values from 0.9 to 1.1).

SUMMARY

Some aspects of the invention include matrices that are suited for forming vessels comprising: a population of endothelial colony forming cells (ECFCs) in a polymerized matrix including at least one fraction of an acid soluble Type I collagen. In some embodiments, these vessels may be formed in vitro while in other embodiments they may be formed in vivo, and in still other embodiments vessel development may begin in vitro and continue after implantation in vivo.

In some embodiments, the fraction of the acid soluble Type I collagen that is used to form the matrix is selected from the group consisting of monomers having an average molecular weight (AMW) of about 282 kDa and oligomers having an AMW of about 603 kDa. In some embodiments, at least some of the fraction of the acid soluble Type I collagen includes a telopeptide reactive aldehyde.

In some embodiments, the matrix further includes a second fraction of the acid soluble Type I collagen that differs from the at least one fraction. In some embodiments, the matrix is comprised of at least one fraction that is an oligomer-rich fraction and a second fraction that is a monomer-rich fraction. In some embodiments, the matrix includes more of the oligomer-rich fraction than of the monomer-rich fraction. The ratios of the oligomer-rich fraction and the monomer-rich fraction may be adjusted to create collagen matrices that have desirable physical and biochemical properties and effects on the development of vacuoles in physical contact with individual ECFCs or populations of ECFCs.

In some embodiments, one or more fractions of acid soluble Type I collagen, or the total amount of acid soluble Type I collagen in a matrix, is present at a concentration of about 0.5 to about 3.0 mg/ml. In some embodiments, the population ECFCs is present in the matrix at a concentration of about $5\times10^5$ to about $2\times10^6$ cells/ml.

Some aspects of the invention include methods of promoting vessel formation comprising the steps of: obtaining an engineered collagen matrix from an oligomer-rich fraction of a Type I acid soluble collagen; and seeding the matrix with a plurality of ECFCs to form one or more vessels within the matrix.

In some embodiments, the matrix is richer in collagen oligomers than collagen monomers. In some embodiments, the AMW of the collagen in the matrix is about 603 kDa. In some embodiments, the AMW of the collagen in the matrix is greater than about 282 kDa. In some embodiments, the AMW of the collagen in the matrix is between about 282 kDa and about 603+/−92 kDa.

In some embodiments, the matrix has a collagen content of about 0.5 to about 3.0 mg/ml. In some embodiments, the collagen content of the matrix is about 0.5 mg/ml. In other embodiments, the collagen content in the matrix about 1.5 mg/ml. In still other embodiments, the collagen content in the matrix is about 3.0 mg/ml.

In some embodiments, the methods of forming vessels include the step of isolating acid soluble oligomers from Type I collagen.

In some embodiments, the matrix used to practice the invention is stiffer than a matrix formed using conventional Type I collagen.

In some embodiments, a stiffness of the matrix may be controlled independently of a collagen concentration of the matrix.

In some embodiments, the matrix is in an unpolymerized state during the seeding step. In some embodiments, the seeding step comprises seeding the matrix with about $5\times10^5$ to about $2\times10^6$ cells/ml.

Some embodiments include the step of implanting the matrix into a diseased area of a patient. In some embodiments, the matrix is implanted after the seeded ECFCs begin to form vessels. In other embodiments, the matrix is implanted before the seeded ECFCs begin to form vessels. The diseased area of the patient into which the matrix and the ECFCs or the matrix with vessels derived from the ECFCs includes an ischemic limb of a human or animal patient in some embodiments.

By regulating cross link formation, a novel mechanism to alter the matrix microenvironment and influence endothelial cell behavior, Type I collagen scaffolds can be engineered to support the formation of long lasting ECFC derived vessels. How collagen matrix microenvironment and physical parameters (matrix stiffness, fibril density, and collagen cross link composition) affect vascular network formation by ECFCs in vitro was investigated. Further how collagen matrix design parameters modulate a matrix-integrin-cytoskeleton signaling axis known to regulate endothelial cell lumen formation was investigated. The results provide information for the development of vascularized tissue constructs that can be controllably delivered to ischemic areas and improve the efficacy of human umbilical cord blood derived ECFC therapies for human subjects.

Collagen building blocks such as oligomers that include a reactive aldehyde and monomers that include a reactive aldehyde and their reactive aldehyde free counterparts can be mixed in various combinations to create a collagen matrix having select bio-mechanical properties. Properties affected by these combinations include the stiffness, matrix pore size, fibril density and the like.

Factors such as the degree of cross-linking and the concentration of collagen in a given mixture of collagen building blocks can be used to influence the fibril density and matrix stiffness of collagen-fibril extracellular matrix. Such matrices can be seeded with ECFC and the judicious use of various compounds that influence cell growth can be used to direct the growth of layers of these cells to form vascular structure. Compounds that can be added to these matrices include, but are not limited to, MT1-MMP, $\alpha_2\beta_1$-integrin, Rac1, Cdc42, and the like.

As disclosed herein factors such as the density of the matrix may affect ECFC vacuole formation. Similarly, the degree of cross linking of the matrix may also affect the degree of vacuole formation. Adjusting parameters that affect ECFC vacuole formation may influence the physical properties of lumen formed from by a given combination of collagen matrix and ECFC.

Surprisingly, the degree of cross-linking in the collagen matrix alters the ECFC mRNA express levels indicating its effect on cellular growth and development. For example, 2 dimensional versus 3-dimensional cell environments alter the cells' morphology and gene expression level and pattern. The activity of the enzyme Rho GTPases in vacuole formation is affected by the matrix. This also appears to the same for the activity and expression levels of other cellular components such as Rac 1 and Cdc42. These results are consistent with integrin cytoskeleton signalling axis affect ECFC capillary morphogenesis.

The level of ECFC seeding within the matrix is positively correlated with the vacuole density of the cells and the bio-structures that they form. Also, increasing the cell density requires that the rigidity of the matrix increase in order to form an increased vacuole area associated with the cells. This is also required in order to increase the total area cell formed structures. Similarly, changing cell density shifts the vacuole area distribution with the cell structures.

Vessels and vascular structures develop via vacuole formation within individual cells, coalescence of these vacuoles into multicellular lumens, and then remodeling via sprouting and branching to form an interconnected network. Exemplary matrices of the present disclosure demonstrated increased vacuole density, vacuole area, and total vacuole area to support and enhance such vessel development.

Some aspects of the disclosure indicate that engineered vascular structures are likely to require a rigid matrix with a low or moderate matrix fibril density (collagen concentration). Such matrices may resist cell traction and degradation while allowing for cell spreading and cell-cell interactions that promote capillary morphogenesis. As disclosed herein, the careful selection of collagen building blocks, ECFC levels and the application of compounds that effect cell growth can be used to control the development of useful vascular structures.

DESCRIPTION

While the novel technology has been illustrated and described in detail in the figures and foregoing description, the same is to be considered as illustrative and not restrictive in character, it being understood that only the preferred embodiments have been shown and described and that all changes and modifications that come within the spirit of the novel technology are desired to be protected. As well, while the novel technology was illustrated using specific examples, theoretical arguments, accounts, and illustrations, these illustrations and the accompanying discussion should by no means be interpreted as limiting the technology. All patents, patent applications, and references to texts, scientific treatises, publications, and the like referenced in this application are incorporated herein by reference in their entirety.

Early in development, a rapidly growing embryo exceeds a size that does not permit appropriate diffusion of nutrients or oxygen sufficiently deep into the organism, requiring the development of a primitive vascular plexus. This process of de novo blood vessel formation known as vasculogenesis [3] allows for development of tissues beyond the diffusion limit of 100-200 μm [4, 5]. Referring now to FIG. 1, the primitive vascular plexus and other vessels are continuously remodeled to accommodate growing or damaged tissues via sprouting and intussusceptive angiogenesis providing a system for transport of not only oxygen and nutrients, but also cytokines and cells throughout the organism. Briefly, during embryonic development mesodermal cells give rise to blood islands which consists of two cell types: angioblasts and hematopoietic elements. The blood islands are part of the primitive vascular plexus which is later remodeled by sprouting and intussusceptive angiogenesis. Recently EPCs have been shown to provide another method of blood vessel formation in the adult via postnatal vasculogenesis.

This vascular system is lined by endothelial cells with a subjacent basement membrane. Small caliber vessels are lined by a single layer of perivascular cells, while larger more complex vessels have a wall comprised of a complex extracellular matrix, nerves, and even smaller vessels. The endothelium is crucial in maintaining normal vessel function. When the ability of the endothelium to repair or generate new vasculature is altered, the result is tissue damage and disease due to either ischemia or inappropriate angiogenesis which can contribute to tumor growth and metastasis. Hence an ability to understand the molecular mechanisms that govern vessel formation and remodeling is of great interest for the treatment of these disease states [5, 6].

The remodeling of the vascular system to repair or generate new vessels involves alterations to the surrounding matrix, cellular migration and proliferation, as well as tightly controlled signaling cascades. As disclosed herein, matrix scaffolds can modulate the in vitro vacuolization and in vivo vessel formation by human endothelial progenitor cells (EPCs) by altering the biophysical environment including mechanical and chemical properties.

Investigation into vasculogenesis and angiogenesis in matrix scaffolds in vitro and in vivo [7-14] has often utilized mature endothelial cell populations such as human umbilical vein endothelial cells (HUVECs) and EPCs from umbilical cord and peripheral blood as well as from human embryonic stem cells (hESCs). The formation of vascular networks for therapeutic applications may require a population of endothelial cells which can be easily isolated, displays a high proliferative potential, and an ability to form vascular networks in vivo. While mature endothelial cell populations such as HUVECs have displayed the potential to form functional vessels in vivo [11, 15, 16], they possess limited proliferative capacity which will prohibit their use in large scale tissue constructs.

EPCs, are known to circulate in the bloodstream and home to sites in need of vessel formation in both physiological and pathological settings, have been examined over the past decade by numerous investigators for their therapeutic potential [17-20]. While studies have demonstrated positive results in animal models, human trials have resulted in mixed success [6, 18]. This may be due, in part, to several factors including: the rarity of the cells [21], controversy in isolation and expansion of EPCs [17, 19, 20, 22-24], and the use of systemic, rather than local delivery [6]. A major limitation has been the lack of a specific marker to identify an EPC and thus, great heterogeneity in the types of cells that have been tested under the guise of an EPC.

During formation of the primitive vascular plexus, angioblasts, which are precursors to endothelial cells [25] are thought to surround emerging hematopoietic elements in close approximation [3]. Isolation of putative EPC populations was originally based on cell surface antigens known to be expressed on hematopoietic stem cells and endothelial cells resulting in isolation of cells of both hematopoietic and endothelial lineages (reviewed in [26]). This method, first described by Asahara et al. [17], was later modified [19, 27] to deplete mature endothelial cells from culture to potentially enrich for EPC. Low density mononuclear cells (MNCs) form adherent colonies, referred to as colony-forming unit-Hill (CFU-Hill) after 5-9 days when plated on fibronectin coated tissue culture surfaces. CFU-Hill cells have been shown to express cell surface antigens consistent with an endothelial cell phenotype, and ingest acetylated low-density lipoprotein (AcLDL), a behavior common to both endothelial cells and monocytes (Table 1). CFU-Hill cells also express several monocyte/macrophage cell surface antigens such as CD14, CD45, and CD115, ingest bacteria, display nonspecific esterase activity, and display limited proliferative potential [8, 17, 28, 29]. Thus, the CFU-Hill assay does not identify EPCs but rather permits enumeration of colonies of hematopoietic cells. While the hematopoietic cells do not directly contribute to the formation of new blood vessels (are not endothelium), these cells do contribute to neoangiogenesis via paracrine signaling pathways and function as circulating proangiogenic cells [30].

Recently another method of EPC isolation has identified a cell population termed endothelial colony forming cells (ECFCs)[23] which are also known as blood outgrowth endothelial cells (BOECs)[22, 31]. Human umbilical cord or adult peripheral blood derived low density MNCs plated on Type I collagen coated tissue culture surfaces form adherent colonies with a cobblestone morphology. These colonies first appear in culture between day 7 and 21, with cord blood derived colonies emerging earlier and at a higher frequency than adult blood derived colonies [23]. Ingram et al. developed a single cell assay to investigate the proliferative capacity of putative EPC populations. ECFCs demonstrated an ability to produce progeny in a clonal fashion, display a hierarchy of proliferative potential, and an ability to give rise to secondary colonies when isolated from both umbilical cord and adult peripheral blood. Consistent with high proliferative behavior ECFC colonies exhibit relatively high levels of telomerase [23]. While ECFCs express cell surface antigens consistent with an endothelial cell phenotype [8, 23], they do not express hematopoietic or monocyte/macrophage cell surface markers such as CD14, CD45, or CD115 [8] (Table 1).

TABLE 1

Phenotypic and functional characterization of CFU-Hill and ECFCs [8]. Von Willebrand factor (VWF), Ulex europaeus agglutinin 1 (UEA-1) lectin, acetylated low-density lipoprotein (AcLDL), vascular endothelial growth factor II receptor (KDR).

| Assay | CFU-Hill | ECFC |
|---|---|---|
| Endothelial surface antigens | | |
| CD31 | 92.31 ± 5.47 | 92.29 ± 1.32 |
| CD105 | 74.36 ± 6.32 | 97.73 ± 1.79 |

TABLE 1-continued

Phenotypic and functional characterization of CFU-Hill and ECFCs [8]. Von Willebrand factor (VWF), Ulex europaeus agglutinin 1 (UEA-1) lectin, acetylated low-density lipoprotein (AcLDL), vascular endothelial growth factor II receptor (KDR).

| Assay | CFU-Hill | ECFC |
|---|---|---|
| CD144 | 34.80 ± 8.74 | 99.15 ± 0.85 |
| CD146 | 56.52 ± 10.00 | 94.21 ± 3.71 |
| KDR | 99.19 ± 0.81 | 68.61 ± 11.26 |
| WWF | 67.21 ± 12.78 | 97.09 ± 2.05 |
| UEA-1 | 41. ± 11.67 | 100 |
| AcLDL | 73.68 ± 9.05 | 99.75 ± 0.25 |
| Hematopoietic surface antigens | | |
| CD45 | 98.15 ± 1.85 | 0.37 ± 0.37 |
| CD44 | 98.53 ± 1.04 | 1.20 ± 0.74 |
| CD115 | 94.42 ± 2.52 | 0.28 ± 0.21 |
| Macrophage properties | | |
| Phagocytosis of bacteria | Yes | No |
| Nonspecific esterase activity | Yes | No |
| Vasculogenic properties | | |
| Proliferative potential | Some | Robust |
| Secondary colony-forming capacity | Some CFU-GM | EC colonies |
| In vivo vessel formation | No | Yes |

One of the original defining concepts of an EPC was that of a circulating cell that possessed postnatal vasculogenic activity; the ability to form a vascular system from a suspension of angioblast-like cells. ECFCs have displayed the potential to form blood vessels de novo in vivo when implanted in a Type I collagen matrix [8, 9] a Matrigel based scaffold [10], or a hyaluronic acid based hydrogel [32]. No other cell type that has been referred to as an EPC can spontaneously form a vasculature in vivo, though many of the hematopoietic derived cells are capable of extravasating from the blood stream, migrating into a tissue, and attaching to any remnants of an endothelial basement membrane that may have persisted after endothelial dropout following cessation of blood flow at a site of ischemia. Thus, the hematopoietic cells that attach to the basement membrane remnant may appear to be forming a vascular structure, but the cells are not synthesizing the matrix to which they are attaching, a necessary step in stabilizing remodeled vasculature [33], and are therefore not endothelial cells. While, ECFCs could be isolated from peripheral blood to provide a patient specific cell source, adult blood derived ECFCs have a decreased proliferative potential [23] and decreased ability to form functional vessels when implanted in a Type I collagen ECM [9] compared to umbilical cord blood derived ECFCs. Thus, ECFCs display all of the properties of a cell that one would envision as an EPC. Unfortunately, circulating ECFCs are extremely rare, being present at a frequency of $1/10^6$ cord blood and $1/10^8$ adult peripheral blood mononuclear cells plated. Furthermore, there is no specific antigen that currently permits prospective isolation of the rare ECFC in the blood stream and discriminates this cell from the occasional viable sloughed endothelial cells derived from the intima of systemic blood vessels.

Another opportunity exists to differentiate EPCs from hESCs. Endothelial cells derived from hESCs have shown the potential to form luminal structures in vitro in both matrigel and Type I collagen scaffolds [34] and functional vessels when implanted in Type I collagen scaffolds in vivo with murine 10T1/2 cells [35]. Additionally, vascular progenitor cells derived from hESCs were shown to form blood vessels when implanted with and without hESC derived smooth muscle like cells in a Matrigel scaffold [36] Additionally, hESC seeded on to poly-(lactic-co-glycolic acid) scaffolds and transplanted between liver lobules of immunodeficient mice were extensively vacsularized by both host and human vessels, suggesting the in vivo differentiation of hESC into EPCs [37].

Additionally, the recent ability to reprogram adult differentiated somatic cells using a defined set of transcription factors to form induced pluripotent cells (iPSCs) could provide a source of patient derived cells for vascularized tissue constructs [38-41]. Recent reports have demonstrated endothelial cells can be differentiated from fibroblast derived human iPSCs [42, 43] which could be a source of autologous cells for angiogenic therapies. However, the proliferative potential of both hESC and iPSC derived endothelial cells has not been fully characterized. Further the ability of iPSC derived endothelial cell to form functional vessels in vivo has not yet been tested and further investigation is needed.

The native extracellular matrix (ECM) is a complex network of structural proteins such as collagen, elastin, fibronectin, and proteoglycans [44]. The engineering of such a complex matrix is very challenging and most approaches have used a simplified matrix as a model of the ECM [44] consisting of either synthetic or biological components. Synthetic matrices used to study angiogenesis and vasculogenesis have been derived from several polymers including polyglycolic acid (PGA), polylactic acid (PLA), polyethylene glycol (PEG) and others. Additionally, combinations of polymers have been used to take advantage of specific properties of each component, such as poly (lactide-co-glycolide) (PLGA). Further, scaffolds from self assembling ionic peptides have been used to study endothelial capillary network formation [45]. One advantage of these synthetic based scaffolds is the ability to fine tune microstructure and degradation profiles by altering the processing and components of the scaffolds [14, 45].

Biological based matrices are typically composed of Type I collagen or fibrin as the main component [44]. Other materials used to generate biological scaffolds to study angiogenesis and vasculogenesis include Matrigel [10], elastin, hyaluronic acid [32, 46], dextran, and alginate [47]. These biological based matrices have the advantage of being bio-compatible, enzymatically degradable, and interacting with host cells to promote vascularization. Scaffolds have additionally been modified to include growth factors [46, 47] and peptide sequences such as arginine-glycine-aspartic acid (RGD) [47] to increase endothelial cell survival and adhesion.

While the ability to tune specific parameters in these scaffolds has been more challenging than for synthetic based scaffolds, methods such as altering source of matrix proteins, combining different biological proteins in scaffolds and cross linking matrix proteins provide potential tools to modulate the biophysical properties. Some studies have demonstrated these effects on biophysical properties of collagen based scaffolds. Collagen source and extraction method has been shown to affect collagen fiber diameter and mechanical properties [48]. Additionally, one report has demonstrated that the addition of hyaluronic acid (HA) to the collagen based scaffolds alters the biophysical properties [49]. Further, chemical fixations such as aldehydes, epoxides, and quinines as well as physical methods such as UV light and dye-mediated photo oxidation can be used to cross link collagen fibrils in vitro [50]. Although these cross linking methods may alter the bio-compatibility of the scaffolds. Finally, Baiely et al. [1] have described how altering the ratio of collagen oligomers and monomers modulated matrix mechanical and microenvironment properties. Further investigation is needed to examine the role of cross linking of matrix components and the addition of various proteins into biological scaffolds on the biophysical properties of these matrices.

Cells embedded in a 3D scaffold bind to and interact with the matrix components. Cells seeded into a collagen based scaffold are able to reorganize the matrix [51, 52]. This interaction appears to occur because the collagen fibrils bind to integrin receptors which are anchored to the actin cytoskeleton [53]. Peptides such as RGD also facilitate scaffold adhesion to integrin receptors on embedded cells. Once bound the integrin receptors cluster and begin to form aggregates of proteins such as talin, vinculin, and α-actinin known as focal adhesions [53, 54]. Focal adhesions serve as the entry point of mechanical cues from the ECM into the cell and these cues influence cell shape, cell migration, cell survival, and cell differentiation [55-57].

The impact of the ECM on cell behavior has been demonstrated for mesenchymal stem cells (MSCs). McBeath, et al., provided evidence that mechanical parameters of the microenvironment dictate MSC shape and lineage commitment [58]. MSCs were plated on a PDMS (polydimethylsiloxane) micropatterned substrate which dictated the extent of cell spreading and shape. WMSCs that exhibited a spread morphology underwent osteogenic differentiation, while MSCs that exhibited a rounded morphology underwent adipogenic differentiation. However, when the cytoskeletal tension was inhibited, MSCs underwent adipogenic differentiation independent of cell shape or morphology [58].

Ruiz and colleagues also demonstrated that force gradients can regulate MSC lineage commitment [59]. MSCs plated on a sinusoidal band where cells cultured on the convex regions experienced high force, while cells grown on the concave regions were exposed to reduced forces. Cells cultured in regions of high force preferentially differentiated down an osteogenic lineage, while cells in the regions of low force underwent adipogenic differentiation. Further osteogenic differentiation could be abrogated by inhibitors of cytoskeletal force generation [59].

Engler, et al., further demonstrated the impact of the microenvironment on MSC behavior by showing that modulating matrix stiffness can direct MSC lineage commitment [60]. Engler, et al., modulated matrix stiffness by altering the concentration of bis-acrylamide cross linking. Three matrix regimes were investigated: a low stiffness matrix that approximated the stiffness of brain, a medium stiffness matrix that was similar to the stiffness of muscle, and a high stiffness matrix that was close to the stiffness of ostcoid. MSCs exhibited characteristics of neurons, muscle cells, and osteocytes on the low, medium, and high stiffness matrix respectively. Further, morphology and lineage specific protein expression of MSCs was dictated by the matrix stiffness supporting the importance of matrix stiffness on cell behavior [60].

The study of angiogenesis and vasculogenesis has evolved over several decades and includes both 2D and 3D assays. While the mechanism of tube formation varies in different assays, all assays have demonstrated that endothelial cell-matrix and cell-cell interactions are crucial for in vitro endothelial cell network formation. One of the first in vitro assays was developed by Folkman and Haudenschild [61] in which endothelial cells formed tubular networks on top of an endothelial cell monolayer. The endothelial cell monolayer secreted its own matrix consisting mainly of Type I collagen which was required for tube formation [62].

In 2D in vitro endothelial cell vessel formation assays, the density of matrix proteins and endothelial cells influence the potential for tube formation. Endothelial cells stimulated by fibroblast growth factor (FGF), known to induce endothelial spreading [63] and endothelial cell tube formation in vitro [64], were plated on non adhesive plates with different density coatings of fibronectin, gelatin, or Type IV collagen [65]. A high density of matrix proteins promoted cell spreading and growth, whereas a low density of matrix proteins resulted in cell rounding and death, but intermediate density resulted in tube formation. Tube formation could be induced at a high matrix protein density by plating endothelial cells at a higher cell density [65].

In 3D assays of in vitro capillary morphogenesis endothelial cells are seeded into a collagen solution so that the cells were evenly distributed in the scaffold [66]. Many studies have investigated the cellular mechanisms of EC lumen formation in 3D Type I collagen scaffolds in vitro [11, 13, 66-76]. These studies have identified a matrix-integrin-cytoskeleton signaling axis that is critical in EC tube formation [66, 69, 73, 75]. Matrix signals enter through integrin receptors and activate Rho GTPase family members Rac1 and Cdc42 to initiate vacuole formation by embedded endothelial cells [75]. Vacuoles then merge and coalesce to form multicellular structures. As these complex structures are forming, the cells are also remodeling the surrounding matrix. Membrane Type I-matrix metalloproteinase (MT1-MMP) dependent proteolysis allows the resident endothelial cells to create vascular guidance tunnels within the scaffold [77]. These channels, once created, allow endothelial cell migration throughout the network of guidance pathways. Interestingly, the integrin ligands which are engaged by the endothelial cells to interact with the scaffold switch during this process. Initially endothelial cells utilize $\alpha 2\beta 1$ for vacuole and lumen formation in 3D collagen scaffolds [66]. As new matrix components are deposited, including fibronectin, laminins, nidogens, and Type IV collagen, the endothelial cells upregulate expression of integrins typically associated with these new matrix components and then use the receptors for migration throughout the network of tunnels [77].

Endothelial cell behavior in 3D scaffolds is altered by the presence of pericytes and other perivascular cells. In vivo vessel formation of ECFCs has been shown to be stabilized by mesenchymal progenitor cells derived from either adult peripheral or umbilical cord blood leading to a longer time of persistence of ECFC derived vessels when implanted in Matrigel [78]. This effect has also been demonstrated in Type I collagen scaffolds. HUVEC derived in vivo vessels were stabilized by MSCs allowing the functional vessels to persist for greater than 130 days. Additionally these HUVEC-MSC composite vessels demonstrated a vasoconstrictive response to endothelin-1 [79]. In vitro investigations have suggested that this stabilization effect could be due to pericyte interaction with endothelial cells within a scaffold inducing endothelial cell basement membrane deposition. Endothelial cells form vascular guidance channels which serve to recruit pericytes to the newly formed vascular networks in vitro. Pericytes induce endothelial cells to deposit basement membrane proteins including fibronectin, laminin, nidogen-1, and perlecan. The deposition of basement membrane components serves to stabilize the vascular structures and diminishes remodeling in vitro [33]. Understanding the role of accessory cells including pericytes, CACs and others will be crucial to development of functional vascular networks.

As outlined above, Endothelial Cell Network Formation studies have focused on the importance of the matrix-integrin-cytoskeleton signaling axis on capillary morphogenesis, only a few studies have investigated the effects of the mechanical properties of scaffolds on endothelial cell tube formation in vitro [70, 74, 80, 81]. Korff et al [70] seeded Type I collagen matrices with endothelial cell spheroids. When two spheroids were placed within 500-700 μm of each other, collagen fibrils were induced to align along the axis between the spheroids. Further, endothelial spheroid sprouts would change direction towards other spheroids, suggesting a role for the matrix of transmitting mechanical signals and aiding in the formation of multi cellular structures before cell-cell contacts are formed. Additionally, soluble RGD peptides, which inhibit collagen fibril-integrin binding, abrogated spheroid sprouting [70].

Sieminski et al. [74] seeded HUVECs or ECFCs into Type I collagen scaffolds with different collagen concentrations. The matrices were either left adhered to the well (adhered) or were released (free floating) to further modify the mechanical properties of the scaffolds. Sieminski noted that changing the collagen concentration altered the matrix stiffness, ligand density, and had other biochemical effects [74]. The average lumen size and tube length of structures were dependent on collagen concentration, endothelial cell type, and whether the matrix was adherent or free floating. ECFCs seeded in 1.5 mg/ml collagen scaffolds that were adherent or free floating caused extreme contraction and cell death. ECFCs in 3 mg/ml collagen matrices formed tube like structures. These structures were shorter and had wider lumens in 3 mg/ml scaffolds that were adherent compared with those that were free floating. HUVECs in 1.5 mg/ml matrices formed structures that were similar to those formed by ECFCs in free floating 3 mg/ml scaffolds, while structures formed by HUVECs in 3 mg/ml scaffolds had an appearance similar to ECFC structures in adherent 3 mg/ml scaffolds. The authors suggest that the ratio of matrix stiffness and cell generated tension are critical in the regulation of capillary morphogenesis [74].

Decreasing stiffness of an ionic self assembling peptide scaffold increases capillary network formation in vitro. HUVECs were seeded into scaffold of stiffness ranging from 46-753 Pa. As stiffness decreased, elongation of capillary structures and the extent of single endothelial cells decreased. At the lowest stiffness tested multicellular capillary structures were seen. Further decrease of scaffold stiffness below 46 Pa led to compaction of the scaffold and did not permit endothelial cell network formation. These results are similar to the results seen in Type I collagen matrices, were compaction of gels at low concentration did not permit for endothelial network formation [45]. These data provide evidence that the matrix microenvironment impacts EC tube formation in vitro.

Scaffold contraction is dependent on cell type in Type I collagen matrices. ECFCs were able to contract the matrices to a greater extent as compared to HUVECs suggesting ECFCs can generate a greater amount of traction [74]. Sieminski speculated that the increased cell traction generated by ECFCs could be due to increased expression of integrins, increased affinity for integrin ligands, increased sensitivity to FGF, or an increased sensitivity to phorbol esters [74].

Increased ECM density decreases capillary morphogenesis in fibrin based scaffolds due to decreased diffusivity and cell generated traction [80, 81]. HUVEC coated dextran beads were seeded into a fibrin scaffold with a monolayer of fibroblasts seeded on top of the matrix. Increasing matrix density reduced sprouting and this negative effect could be overcome by seeding the fibroblasts within the matrix. The authors demonstrated an inverse relationship between matrix density and diffusive transport of fluorescently conjugated mass markers. These results suggest that decreased diffusion of cytokines could be responsible in part for the decreased capillary morphogenesis with increased matrix density [80]. Kniazeva et al. demonstrated that chemical inhibitors of cell generated traction decreased sprouting of HUVECs into the fibrin matrix and that this inhibition was directly proportional the matrix density [81]. These results further support the idea that the ratio of cell traction and apparent matrix stiffness is an important regulator of capillary morphogenesis.

Capillary morphogenesis occurs via vacuole formation within individual cells, coalescence of these vacuoles into multicellular lumens, and then remodeling via sprouting and branching to form an interconnected network [90]. Several studies have identified cellular processes, the molecular pathway, and associated cytokines involved in this process [90, 117-120]. From these studies it is evident that outside in signaling through a matrix-integrin-cytoskeleton signaling axis regulates capillary morphogenesis in collagen based extracellular matrices. The interaction of the endothelial cells and the extracellular matrix during vessel formation is initiated by integrin binding to collagen fibrils, resulting in integrin clustering, focal adhesion formation, cell generated traction and collagen fibril contraction and reorganization [89-93]. The remodeling of the ECM is resisted by the collagen fibril network. The resulting cell-matrix force balance determines the extent of capillary morphogenesis [1, 74, 121] suggesting that that the biophysical and biochemical properties of the matrix are integral in regulating capillary morphogenesis.

While in vitro evidence suggests that physical properties of Type I collagen matrices including fibril density and stiffness influence endothelial cell capillary morphogenesis [70, 74, 99], the effect of matrix physical properties has only recently begun to be studied on endothelial colony forming cells (ECFCs) in vivo vessel formation. Collagen fibril density and stiffness impact human ECFC vasculogenesis in vivo [122] and Matrigel stiffness alters host capillary invasion [123]. Scaffolds with distinct biophysical environments were created with different shear storage moduli (stiffness) and fibril densities by altering the collagen concentration. While human and total vascular density was greater in scaffolds with lower collagen concentrations and shear storage moduli, vascular area, which was dependent upon both vessel size and density, increased with increasing collagen concentration and shear storage modulus. [122]. Additionally, Matrigel was implanted subcutaneously in mice with varied matrix stiffness (700-900 Pa), with 800 Pa scaffolds resulting in increased level of host capillary in growth [123]. While it is likely that complex processes such as angiogenesis and vasculogenesis are regulated by a multitude of factors, these results suggest that increasing matrix stiffness and matrix density results in increased vascularization in vivo.

While the above studies demonstrate a role of matrix stiffness and matrix density in capillary morphogenesis, additional matrix properties are important in regulating tissue properties that have the potential to alter cell behavior and vessel formation. The ability of Type I collagen to form the extracellular matrix of tissues with such distinct functions as skin and bone is due largely to alterations in post translational modification and intermolecular-cross links. This can be seen by the different collagen cross link chemistries that predominate in soft tissue such as skin, sclera, and the cornea as opposed to stiff tissues such as bone, cartilage, and tendons [124]. Two enzymes lysyl hydroxylase and lysyl oxidase regulate cross link formation. During the assembly of individual collagen monomers into fibrils, lysyl oxidase catalyzes the formation of covalent cross links to form oligomers [125].

Figure 2:
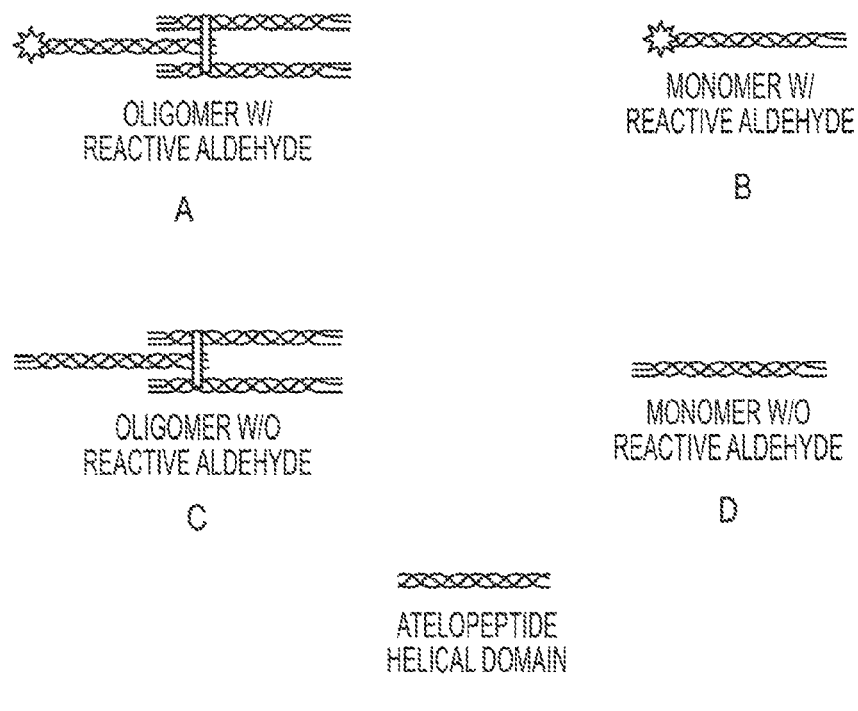
FIG. 2. Illustration of different forms of collagen isolated from native collagen by an acid extraction process.

Referring now to FIG. 2, acid-extraction from tissues results in the isolation of both monomers (FIG. 2, Panel B) and cross linked oligomers (FIG. 2, Panel A). These molecules have reactive aldehydes resulting from acid labile divalent cross links, which will reform covalent cross links upon polymerization. Asterisks denote reactive aldehydes that form covalent cross links and red lines denote native, non labile covalent cross links. These reactive aldehydes can be eliminated by chemical reduction to alter the ability of these molecules to form cross links upon polymerization (FIG. 2, Panels C-D). The ability to alter cross link formation can be further inhibited by proteolytic digestion with pepsin to remove the telopeptide domains required for cross link formation, resulting in atelo-oligomers and atelo-monomers (FIG. 2, Panel E).

Figure 3:
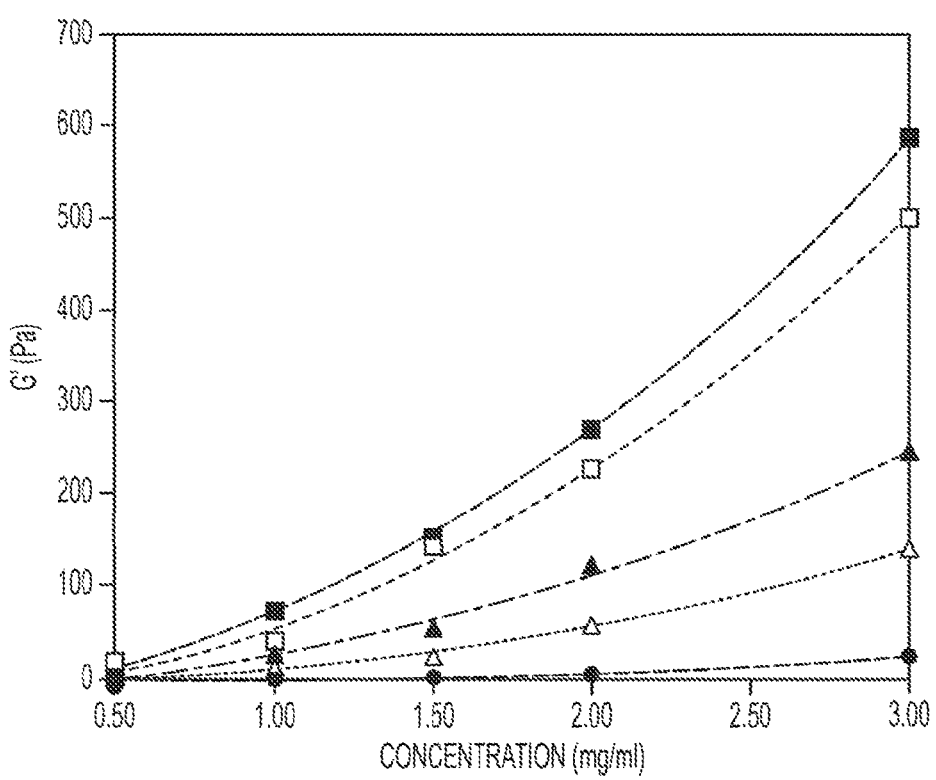
FIG. 3. Graph of shear storage modulus (G') versus collagen concentration measured with collagen matrices comprised of varying levels of collagen monomer and oligomer.

The Voytik-Harbin laboratory has demonstrated that these unique collagen building blocks can be used to polymerize matrices with varied G' (Shear storage modulus) versus collagen concentration profiles. Referring now to FIG. 3, a graph is provided illustrating that collagen molecules yield polymerized matrices with distinct relationships between Shear storage modulus (G') and collagen concentration. Oligomer with reactive aldehyde (closed square), oligomer without reactive aldehyde (open square), monomer with reactive aldehyde (closed triangle), monomer without reactive aldehyde (open triangle), and pepsin digested oligomer (filled circle).

It has also been demonstrated that mixing monomer-rich and oligomer-rich fractions in different proportions, which was quantified by average polymer molecular weight (AMW), alters the matrix microenvironment and physical properties. Increase in AMW resulted in a decrease in matrix pore size (FIG. 4), but an absence of a positive correlation in fibril diameter or fibril density (FIG. 5). Additionally AMW was positively correlated with matrix stiffness (G') and compressive modulus (Ec) (FIG. 5) [1].

Figure 4:
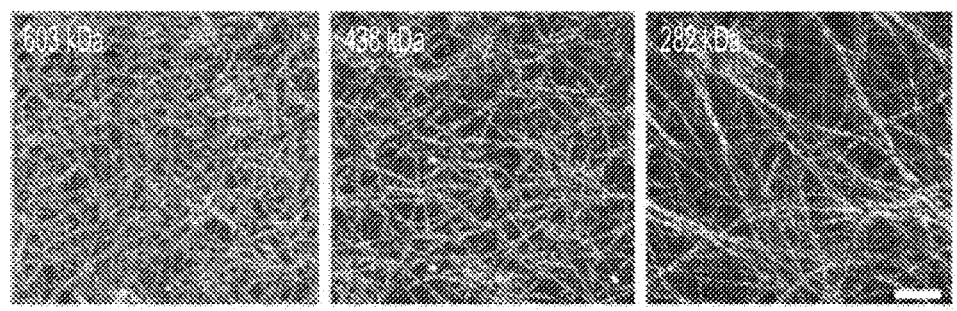
FIG. 4. Photomicrographs of collagen matrices comprised on different levels of AMW.
Figure 5A:
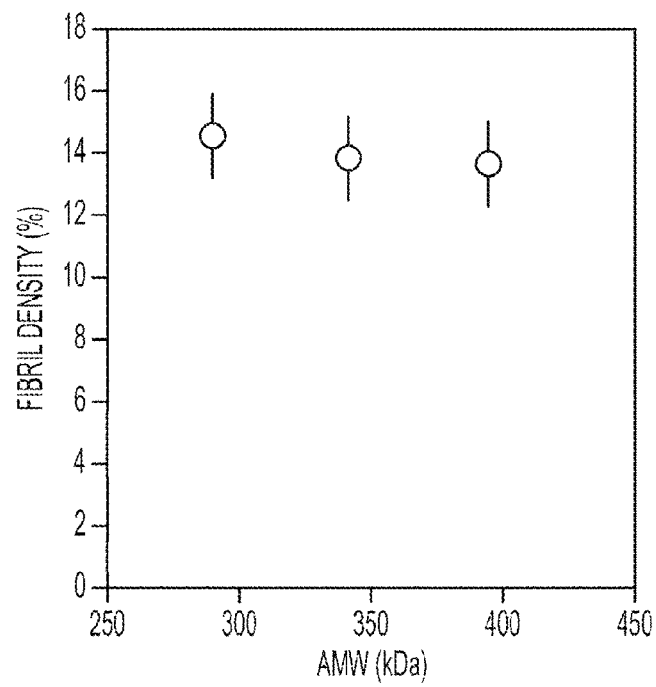
FIG. 5A. Graph of Fibril Density versus AMW (kDa).

Referring now to FIG. 4, photomicrographs are provided illustrating the projected pore size decreases with increasing AMW. All matrices were polymerized with a collagen concentration of 0.7 mg/ml and under the same conditions. 2D projections represent a total image thickness of 10 μm (101 slices, scale bar=10 μm) [1].

In this study PSC oligomer-rich and monomer-rich fractions were used to polymerize matrices with altered biophysical properties to determine the role of collagen concentration, stiffness, and cross link chemistry on ECFC vacuolization. Importantly this allows for an uncoupling of or independent control over matrix stiffness and collagen concentration (fibril density), which has previously confounded investigations into their role in vascular network formation. Further the role of a matrix-integrin-cytoskeleton signaling axis previously demonstrated to regulate endothelial capillary morphogenesis in collagen based matrices in ECFC vacuole formation was tested and shown to be altered by the matrix microenvironment. Finally, the role of cell density in capillary morphogenesis in matrices with varied microstructure and biophysical properties was examined and supports a role for the relevance of a cell-matrix force balance in determining the extent of capillary morphogenesis. The approach proposed here is the first to detail the separate contributions of these two different matrix parameters in modulating ECFC behavior in vitro. This will provide new information that will allow for a better understand of the underlying mechanisms of ECM-ECFC interactions. Importantly, this information is critical for the design and development of vascularized tissue constructs that can be controllably delivered to ischemic or other diseased areas and improve the efficacy of human umbilical cord blood derived ECFC therapies.

Therapeutic vasculogenesis, de novo blood vessel formation from individual endothelial cells, is a potential strategy to improve these regenerative medicine therapies. Further ECFCs, an endothelial progenitor cell population with clonal proliferative potential, have demonstrated an ability to form functional vessels in vivo when implanted in collagen based scaffolds [8, 9, 78, 122]. However, the cellular response of ECFCs to biophysical and biochemical cues in the ECM has only recently been explored.

Previous studies have demonstrated a role for matrix stiffness and matrix density in capillary morphogenesis [81, 96, 122, 130]. As reported herein there is a surprising role for both matrix stiffness and matrix density the regulation of ECFC vacuole and lumen formation. A report by Bailey, et al. [1] found a differential response of ECFC vacuole formation to matrices polymerized from monomer and oligomer rich fractions. The instant disclosure demonstrates a role for collagen cross link composition, by altering the oligomer content in collagen based scaffolds, in modulating ECFC vacuole formation in vitro. By altering the oligomer content of the collagen scaffold the collagen concentration and shear storage modulus (stiffness) could be independently varied, allowing their impact on ECFC vacuole formation to be investigated. The process of capillary morphogenesis in this system was shown to depend upon a previously described matrix-integrin-cytoskeleton signaling axis involving integrin signaling and downstream RhoGTPase activity. Additionally alteration in collagen cross link composition was shown to alter both mRNA and protein expression by ECFCs during in vitro vacuole formation and is the first to show alterations in FAK signaling during vacuole formation. Finally cell density was shown to alter ECFC vacuole formation dependent upon the matrix biophysical properties, supporting the role for cell-matrix force balance in vessel formation.

ECFC vacuole density, vacuole area, and total vacuole area increased with increasing collagen concentration. This was in part due to a shift in vacuole distribution toward larger vacuoles. These results are consistent with previous reports that altered matrix density alters in vitro capillary morphogenesis. However, previous reports have found that increased matrix density leads to decreased endothelial lumen formation. These differences could be due to the use of lower cell seeding density [74] and matrix composition such as peptide [45] or fibrin based scaffolds [80, 81]. In the present study at a cell seeding density of $5 \times 10^5$ cells/ml ECFC total vacuole area decreased with increasing collagen concentration. Additionally ECFCs have been shown to exhibit increased matrix contraction and cell elongation compared to other endothelial cell populations [130]. Thus the ECFCs may exert greater cell traction requiring more matrix resistance to drive vacuole formation. It is possible that these different results based on cell seeding density, endothelial cell source, or matrix compositions between various studies are due to alterations in the cell-matrix force balance.

As disclosed in Bailey, et al. [1] that collagen cross link chemistry alters ECFC vacuole formation in vitro. As reported here in ECFCs seeded into matrices polymerized from oligomer rich fractions demonstrated increased vacuole density, vacuole area, and total vacuole area compared to ECFCs cultured in monomer rich matrices. This was due in part to an altered vacuole area distribution, with ECFCs cultured in oligomer rich matrices displaying a shift in the distribution toward larger vacuole areas. Increased oligomer content in matrices polymerized with a matched shear storage modulus (stiffness) of 200 Pa or matched collagen concentration of 1.5 mg/ml resulted in increased ECFC vacuole density and total vacuole area. Finally, oligomer rich and monomer rich matrices with matched collagen concentrations of 0.5, 1.5, and 3.0 mg/ml were polymerized and seeded with ECFC. At each collagen concentration the oligomer rich matrix demonstrated increased ECFC vacuole density and total vacuole area.

The differences in cell behavior in the different oligomer rich and monomer rich matrices suggest the importance of multiple biophysical properties in regulating ECFC vacuole formation. Oligomer rich matrices have a lower collagen concentration than monomer rich matrices with the same stiffness. Additionally, oligomer rich matrices have a higher stiffness that monomer rich matrices polymerized with the same collagen concentration. Together these data suggest that a rigid matrix with low fibril density (collagen concentration) is supportive of ECFC vacuole formation. The ability to generate these characteristics in a matrix is dependent upon the ability to modulate the collagen cross link composition to increase interfibril branching which has been shown to contribute to the matrix stiffness [131]. In this way the matrix is able to resist cell traction and degradation, while allowing for cell spreading and cell-cell interactions necessary for capillary morphogenesis to occur. These results further suggest that collagen derived from varied tissue sources which display different cross link chemistries could be used to polymerize matrices with a wide range of biophysical cues to guide ECFC vacuole and lumen formation.

Previous work has detailed the role of a matrix-integrin-cytoskeleton signaling axis [132] in endothelial capillary morphogenesis. This axis involves integrin binding to collagen fibrils leading to downstream RhoGTPase signaling and MMP mediated matrix degradation and remodeling. The use of specific chemical inhibitors of β1 integrin, Cdc42, Rac1, and MT1-MMP showed that this signaling axis is involved in ECFC vacuole formation in vitro. While all inhibitors led to a reduction in total vacuole area, the inhibition of Cdc42 led to reduction in total vacuole area by decreasing vacuole density, while the inhibition of Rac1 decreased total vacuole area by decreasing the average vacuole area. These results suggest that Cdc42 is intimately involved in the initiation of vacuole formation, while Rac1 is involved in the enlargement and remodeling of the vacuoles. Thus it is possible that these molecules could be used to either inhibit the initiation of vasculogenesis or the continued remodeling of a primitive capillary network. Further investigation into the nuanced role of these molecules in vacuole formation particularly in vivo is required.

Endothelial cell behavior in traditional 2D tissue culture plastic is different than in 3D environment seen in tissue scaffolds and in vivo environments. ECFC mRNA expression of Cdc42, Rac1, and MT1-MMP, three genes known to play a role in capillary morphogenesis, were shown to be up regulated in 3D collagen based matrices compared to culture on 2D tissue culture plastic. These differences are not unexpected based on the differences in cell morphology in the different environments. Sacharidou et al. [128] have previously demonstrated that Cdc42 and MT1-MMP activity is necessary for endothelial cell migration through collagen matrices by not on 2D surfaces, suggesting that Cdc42 and MT1-MMP play a significant role in endothelial cell 3D but not 2D behavior. This may in part explain why the mRNA levels are up regulated in 3D culture as ECFC begin to undergo capillary morphogenesis and require active Cdc42 and MT1-MMP to initiate the process.

In order to determine if collagen concentration and cross link chemistry, which altered ECFC vacuole formation, altered cell signaling, RNA was isolated from ECFCs seeded in 3D matrices. While collagen concentration did not demonstrate an effect on mRNA expression, collagen cross link composition did alter the expression of Cdc42, Rac1, and MT1-MMP transcript levels. ECFCs cultured in oligomer rich matrices displayed increased expression of Cdc42 and MT1-MMP and reduced expression of Rac1 mRNA compared to ECFC cultured in monomer rich scaffold. These data suggest that Cdc42 and MT1-MMP mRNA expression is increased as the ECFC are undergoing capillary morphogenesis. Rac1 mRNA expression is increased in monomer rich matrices which yield reduced ECFC vacuole formation. This increase in Rac1 expression may be the result of the multiple roles of Rac1 in cell behavior [133]. Rac1 is known to be involved in cell migration [133, 134] and the endothelial cells that do not undergo capillary morphogenesis do exhibit an elongated morphology. It is possible that in this environment the cells migrate throughout the matrix instead of initiating vacuole formation and that cell migration requires higher levels of Rac1 than does vacuole formation. It is interesting to note that collagen concentration does not alter ECFC mRNA expression of Cdc42, Rac1, and MT1-MMP even though it alters vacuole formations. One possible explanation for this is that there is a different level of active protein expressed in the different collagen concentrations. The FRET based RhoGTPases shown to be involved in ECFC vacuole formation in this study represent an ideal system to further investigate the protein expression levels in capillary morphogenesis at different collagen concentrations.

These results suggest that FAK protein levels are increased in ECFC cultured in oligomer rich matrices. FAK levels were shown to be increased in oligomer rich matrices compared to monomer rich matrices at either matched collagen concentration of 3.0 mg/ml or matched stiffness of 200 Pa. Previous work has demonstrated a mechanotransduction signaling pathway though β1 integrin and Src [135] to RhoGTPases during capillary morphogenesis. This data extends that signaling pathway to include FAK. It is not surprising that a matrix which is more supportive of vacuole formation would increase FAK expression as this molecule is known to be involved in focal adhesion formation and signaling with integrin receptors to the cytoskeleton [136, 137]. It further suggests FAK as a potential target to modulate vessel formation in future studies.

The results of this study have demonstrated a role for matrix stiffness, matrix density, and collagen cross link chemistry in regulation in vitro vacuole formation. Each of the variables plays an important role in determining the microenvironment that the encapsulated endothelium experiences and responds to. Previous work has also demonstrated a role for cell-matrix force balance in capillary morphogenesis [74, 80]. To begin to test if the cell generated tension was also responsible for altering vacuole formation, ECFCs were seeded in collagen scaffolds at either $5 \times 10^5$ cells/ml or $2 \times 10^6$ cells/ml and vacuole formation was analyzed. While increasing cell density resulted in elevated vacuole density it reduced average vacuole area, and resulted in no difference in total vacuole area. While ECFCs seeded into matrices polymerized at 0.5 and 3.0 mg/ml from monomer rich fractions and 0.5 mg/ml from oligomer rich fractions demonstrated similar results, ECFCs seeded into 3.0 mg/ml matrices demonstrated increased vacuole density, average area, and total area. Additionally the vacuole distribution for ECFCs seeded into the monomer and 0.5 mg/ml oligomer matrices displayed a shift to the left, while ECFCs seeded into the 3.0 mg/ml oligomer matrix displayed no such shift. These data suggested the possibility that the ratio of matrix stiffness and cell tension was being altered by the increased cell density and that the monomer and 0.5 mg/ml oligomer matrices were unable to sufficiently resist cell traction and remodeling leading to stagnation in vacuole formation. This warrants additional investigation possibly by directly altering the cytoskeleton contractility using an agonist such as lysophosphatidic acid (LPA) or an antagonist such as Blebbistatin.

The results disclosed herein clearly show that the biophysical properties of collagen based matrices, specifically collagen concentration, stiffness, and cross link composition modulate ECFC vacuole formation in vitro. Additional, results provided herein, demonstrate the role of cell matrix force balance in driving in vitro capillary morphogenesis. Further demonstrating that the signaling cascade regulating this process is altered by changes in the matrix microenvironment. It is likely that all of the matrix design parameters described here will impact in vivo vasculogenesis, and allow for the development of therapeutically relevant strategies to deliver ECFCs to damaged or diseased tissues.

Experimental Section

Culturing of ECFC

Human umbilical cord blood derived ECFCs were isolated and cultured as previously described [23]. ECFCs were used between passage 5 and 10 for all experiments.

Separation of Collagen into Monomer-Rich and Oligomer-Rich Fractions

Type I collagen, comprising monomers and oligomers, was isolated from pig skin (PSC) and solubilized in acetic acid (0.005 M) to achieve a desired collagen concentration (4 mg/ml). Subsequent fractionation of PSC into monomer-rich and oligomer-rich formulations was performed by adding an equal volume of 2× solubilization buffer (0.06 M phosphate, 0.2 M NaCl, and 1.2 M glycerol, pH 7.0) with mixing. The solution was left to stand at 30° C. for 7 days.

At desired times, the solution was then centrifuged at 10,000 rpm and 4° C. for 10 minutes and decanted and the supernatant was retained. At each time point, the supernatant represented the monomer-rich collagen fraction and the pellet represented the oligomer-rich collagen fraction. The pellet was then resolubilized in 0.1 M acetic acid and the resolubilized pellet and the supernatant were dialyzed against 0.01 M acetic acid and lyophilized to dryness.

Figure 19:
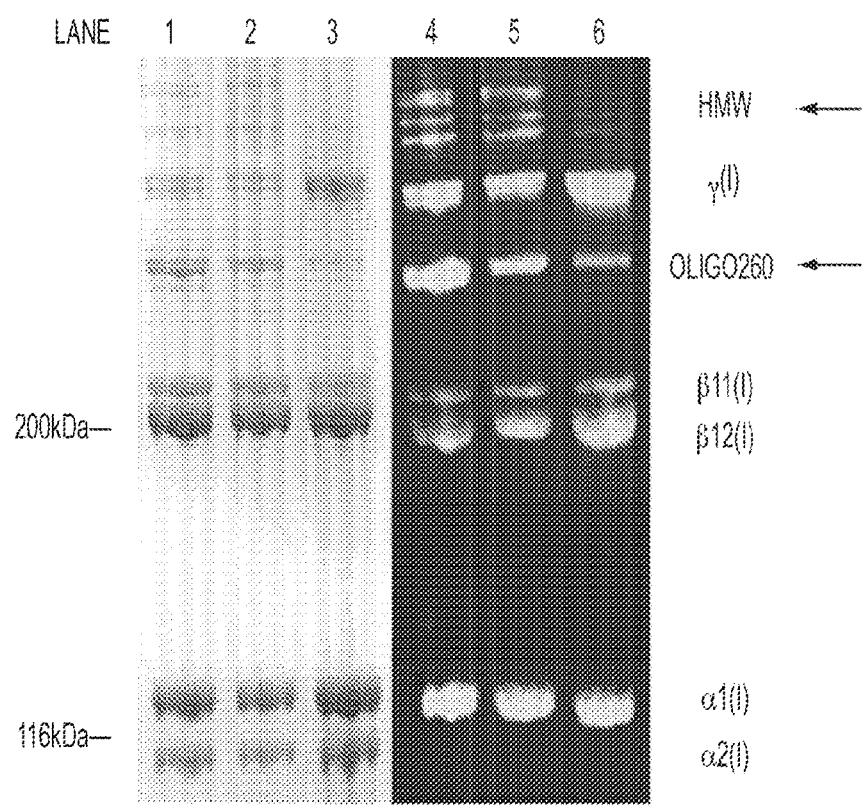
FIG. 19. Sulfate polyacrylamide gel electrophoresis (SDS-PAGE) (4%) analysis (Lanes 1-3) and Western blot analysis with a collagen $\alpha 1(I)$ antibody (Lanes 4-6) of a Type I collagen starting material, an oligomer-rich collagen fraction, and a monomer-rich collagen fraction.

The composition of the oligomer-rich and monomer-rich collagen fractions were confirmed by sulfate polyacrylamide gel electrophoresis (SDS-PAGE) (4%) analysis (FIG. 19, Lanes 1-3) and Western blot analysis with a collagen α1(I) antibody (FIG. 19, Lanes 4-6). In FIG. 19, the unfractionated, PSC starting material is represented in Lanes 1 and 4, the oligomer-rich collagen fraction is represented in Lanes 2 and 5, and the monomer-rich collagen fraction is represented in Lanes 3 and 6.

SDS-PAGE analysis showed that, in addition to the α1(I), α2(I), β11(I), β12(I), and γ(I) bands routinely observed in denatured purified collagen Type I preparations, the PSC included a prominent band corresponding to a molecular weight of 260 kDa (Oligo 260) as well as high molecular weight (HMW) components with molecular weights greater than 300 kDa (FIG. 19, Lane 1). The β, Oligo260, γ, and HMW bands represent two or more a chains that are covalently linked by natural collagen crosslink chemistries, whereas the α1(I) and α2(I) bands, which are present at a ratio of 2 to 1 respectively, represent component polypeptide chains (~100 kDa) within a single triple helical collagen molecule. The Oligo260 and HMW components were retained at significant levels in the oligomer-rich fraction and found at substantially reduced levels in the monomer-rich fraction, suggesting that the Oligo260 and HMW components represent oligomer derivatives with intermolecular cross-links.

Western blot analysis used mouse monoclonal antibodies specific for Type I (AB6308, Abcam, Cambridge, Mass.) and Type ITT (MAB 1343, Chemicon, Temecula) collagen. According to manufacturer's specification, the antibody for Type I collagen was developed against the full length native protein. However, in the present study, this antibody showed specificity to the α1(I) chain when applied to denatured collagens. Western blot analysis confirmed that α1(I), β11(I), β12(I), Oligo260, and HMW components contained the epitope for collagen α1(I) (FIG. 19, Lane 4).

Also, intrinsic viscosity measurements, which provide a measure of the AMW of collagen polymer solutions in their native, undenatured state, were performed. In brief, apparent viscosities of collagen solutions in 0.01N HCl were measured on an AR2000 rheometer (TA Instruments, New Castle, Del.) with a cone geometry (40 mm, 2° cone angle). Viscosities for solutions representing collagen concentrations of 0.1-0.3 mg/ml were measured at shear rates of 100-1500 s at 10° C. The AMW was calculated using the Mark-Houwink equation, $|\eta|=kM^a$, where a=1.8 and k was determined for each shear rate assuming a monomer-rich AMW of 282 kDa. AMW was extrapolated to zero shear rate. Intrinsic viscosity measurements indicated that monomer-rich fractions had an AMW value of about 282 kDa and oligomer-rich fractions had an AMW value of about 603+/−92 kDa. These results confirmed the prominence of cross-linked collagen monomers within the oligomer-rich fraction. PSC yielded roughly four times more oligomer-rich collagen compared to monomer-rich collagen, based upon dry weight.

The monomer-rich and oligomer-rich fractions described above were also recombined at different ratios to create collagen formulations that varied in monomer/oligomer content and thus AMW.

Additional information regarding the separation of collagen into monomer-rich and oligomer-rich fractions is set forth in U.S. Patent Application Publication No. 2008/0268052 to Voytik-Harbin et al., the entire disclosure of which is expressly incorporated herein by reference, and is described in [1].

Polymerization of 3D Collagen Matrices

Matrices were polymerized as previously described [1]. Briefly ECFCs were seeded at 5×105 or 2×106 cells/ml into unpolymerized collagen solution and allowed to polymerize for 30 min at 37° C. and 5% CO2 and then 120 µl of warm EBM-2 (Lonza, Basel, Switzerland) supplemented with 40 ng/ml FGF and SRII [126] was added. Media was changed at 24 hours. For vacuole formation assays, matrices were set in duplicate and at least three independent experiments were conducted.

Figure 5B:
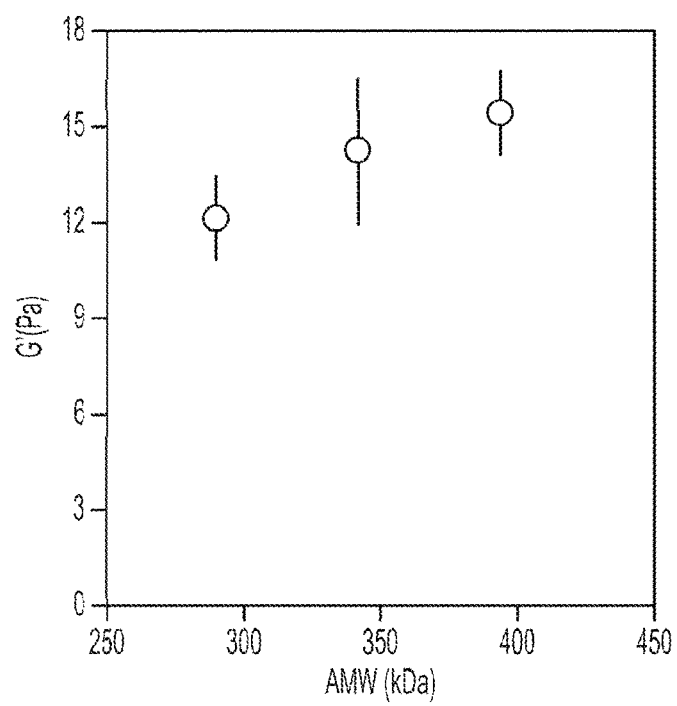
FIG. 5B. Graph of G' (Pa) versus AMW (kDa).
Figure 5C:
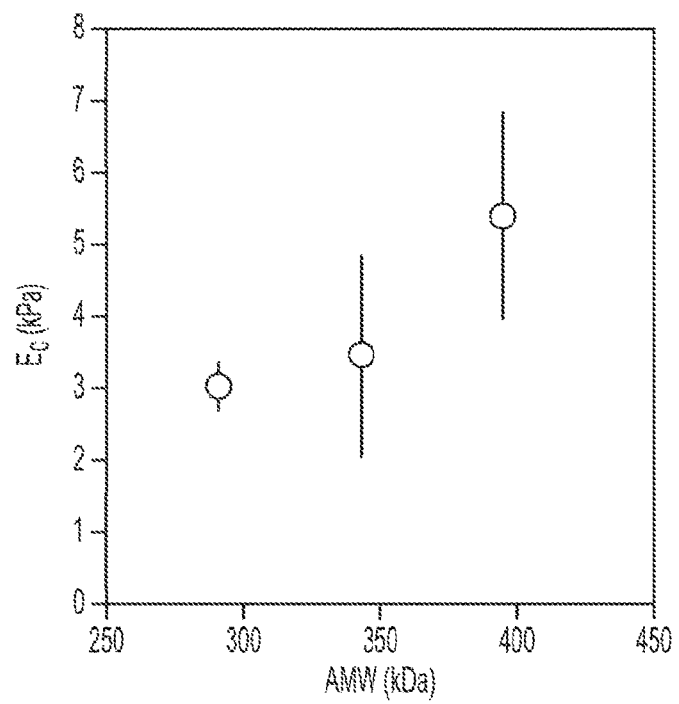
FIG. 5C. Graph of Ec (kPa) versus AMW (kDa).

Referring to FIGS. 5 A-C. Fibril density did not demonstrate a positive correlation with AMW, while G' (FIG. 5B) and Ec (FIG. 5C) increased linearly with increasing AMW. Data represent mean±SD [1].

Toluidine Blue Staining of Collagen Matrices

For analysis of in vitro vacuole formation, cultures were fixed with 4% paraformaldehyde for 20 minutes at 48 hours. Scaffolds were stained with 0.1% toluidine blue 0 in 30% methanol for 20 minutes and then washed with PBS.

Analysis of In Vitro Vacuole Formation

A Leica DM IRE2 microscope (Leica Microsystems, Bannockburn, Ill.) with attached Retiga 4000R digital camera (QImaging, Surrey, BC, Canada) was used to image the entire area of each matrix using a 10× objective and the middle 9 fields of view were used for analysis. Lumens were quantified using a standard image analysis system Metamorph (Molecular Devices, Sunnyvale, Calif.). From these data average lumen area and total lumen area were calculated. Lumens were defined as areas completely surround by a toluidine blue labeled endothelial cell membrane.

Perturbation of ECFC Vacuole Formation

Chemical inhibitors TIMP-3 (5 µg/ml, R&D Systems, Minneapolis, Minn.), Casin (2.5 µM), NSC23766 (25 µM), or MAB17781 (1 µg/ml, R&D Systems, Minneapolis, Minn.) were added into the media during ECFC culture in 3.0 mg/ml matrices polymerized with the oligomer rich fraction. Treatments were conducted in duplicate and at least three independent experiments were conducted.

mRNA Isolation

After 48 hours of cultures, RNA was isolated from ECFCs seeded into collagen matrices using a RNeasy Mini kit (Qiagen, Valenci, Calif.). Ten matrices were pooled from each treatment group for an experiment. At the same passage, RNA from ECFC grown on tissue culture plastic was isolated. Three independent experiments were conducted. All RNA samples were quantified using a Nanodrop 1000 (Thermo Scientific). RNA quality was determined by the A260/A280 and A260/A230 ratios. Using reverse transcription cDNA was synthesized using SuperScript II Reverse Transcriptase (Invitrogen, Carlsbad, Calif.).

Quantitative Real Time RT-PCR (qRTPCR)

Quantitative real time RT-PCR was performed using custom designed primers (Invitrogen, Carlsbad, Calif.) for the three genes of interest (Table 2), FastStart Universal SYBR Green Master (Roche) and a ABI7500 Real-Time PCR system (ABI, Carlsbad, Calif.). Cycling conditions were as follows: 95° C. for 10 minutes, followed by 40 cycles of 95° C. for 15 seconds and 60° C. for 1 minute. 7500 Software (ABI, Carlsbad, Calif.) was used to determine the CT values. Data was analyzed using the 2-ΔCT method using ATP5B as a reference gene. Each sample was run in triplicate two separate times and a maximum standard deviation between CT values of triplicates of 0.3 was considered acceptable.

Western Blot

Protein was extracted from ECFCs seeded into collagen scaffolds after 48 hours of culture. Total cellular extracts were electrophoresed by sodium dodecyl sulfate-polyacrylamide gel electrophoresis (SDS-PAGE), transferred to nitrocellulose and probed with anti-FAK (H-1, sc-1688 Santa Cruz Biotechnology, Santa Cruz, Calif.).

ECFC Transfection

Three FRET based Rho GTPases, RhoA, Rac1, and Cdc42 plasmids, were used for these experiments. ECFCs were transfected by electroporation using a Neon Transfection Device (Invitrogen, Carlsbad, Calif.) following the manufacture's recommended parameters. Briefly, 1×10⁷ cells/ml were transfected using 1 µg/ml plasmid, a pulse voltage of 1000 mV, a pulse width of 20 ms, and a pulse number of 2.

Transfected ECFC Microscopic Imaging

Transfected ECFCs were imaged by DIC and fluorescence microscopy with a Nikon microscope (Nikon, Tokyo, Japan) using a 40× oil immersion objective. Excitation wavelengths for the cyan fluorescence probe (CFP) and the yellow fluorescence probe (YFP) were 475 nm and 535 nm respectively. Images were processed using NIS elements imaging software (Nikon, Tokyo, Japan) using iterative deconvolution and automatic background subtraction to improve resolution and remove image noise.

Statistical Analysis

All values are presented as mean±standard error (SE). Analysis of variance was conducted using SAS statistical software (SAS Institute, Inc., Cary, N.C.) to determine if there was a significant effect of the variable of interest on cell behavior. If a statistically significant relationship was found Tukey's test for multiple comparisons was used to determine which groups were significantly different or a two-tailed student's t-test was used to evaluate the significance between two groups. Additionally, a Dunnett's post test was used to compare treatment groups to a control group. A p-value of less than 0.05 was considered significant.

Figure 6:
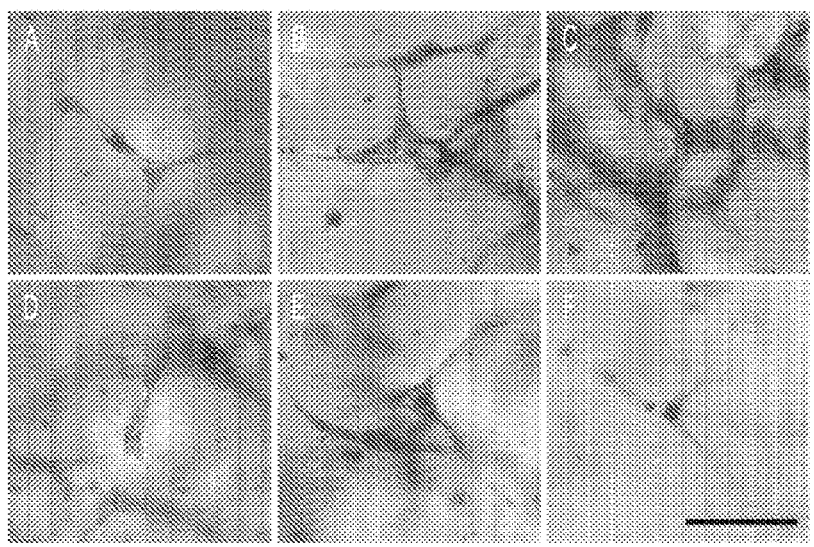
FIG. 6. Photomicrographs of ECFCs seeded into collagen matrices.
Figure 7A:
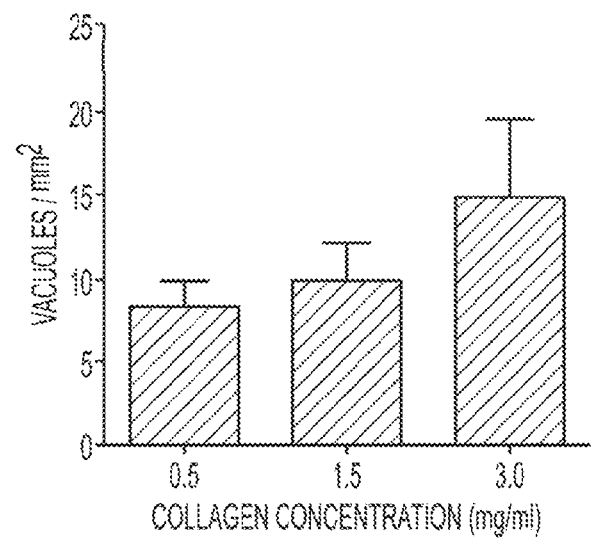
FIG. 7A. Graph of Vacuole Area ($mm^2$) versus Collagen Concentration (mg/ml).
Figure 7B:
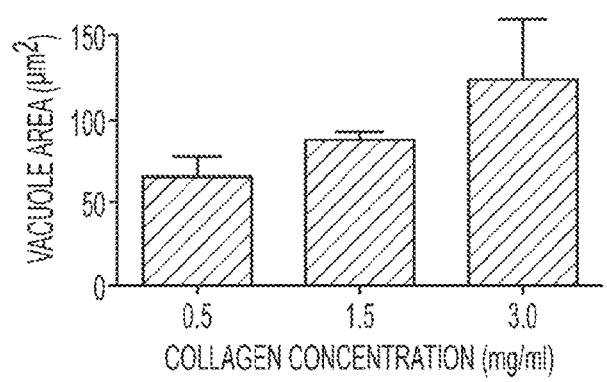
FIG. 7B. Graph of Vacuole Area ($mm^2$) versus Collagen Concentration (mg/ml).
Figure 7C:
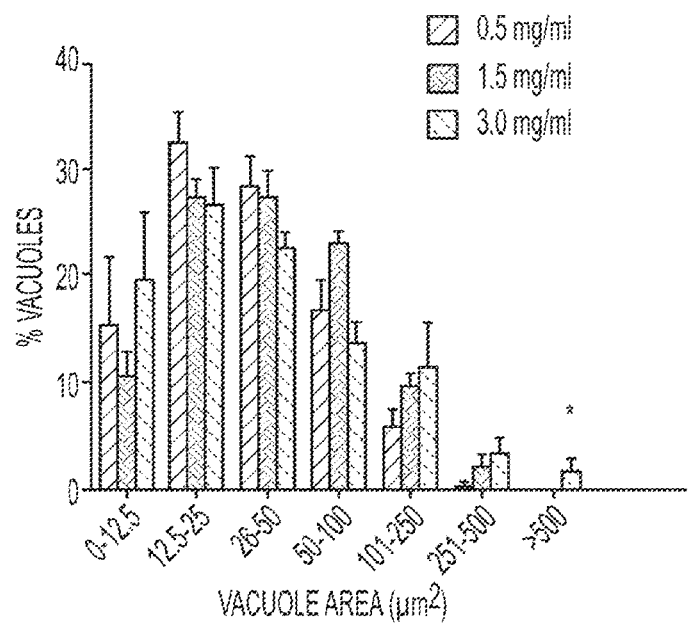
FIG. 7C. Graph of Percent Vacuole (%) versus Vacuole Area ($mm^2$).
Figure 7D:
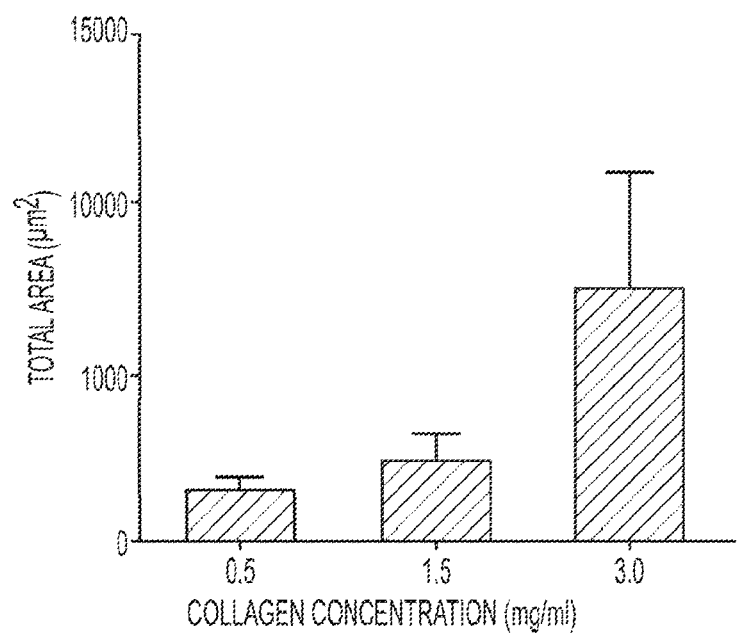
FIG. 7D. Graph of Total Area ($mm^2$) versus Collagen Concentration (mg/ml).
Figure 8A:
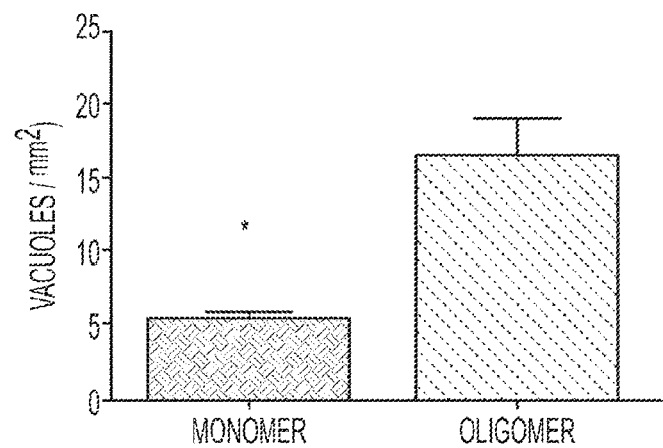
FIG. 8A. Graph of Vacuoles/$mm^{-2}$ measured with monomers or oligomers.
Figure 8B:
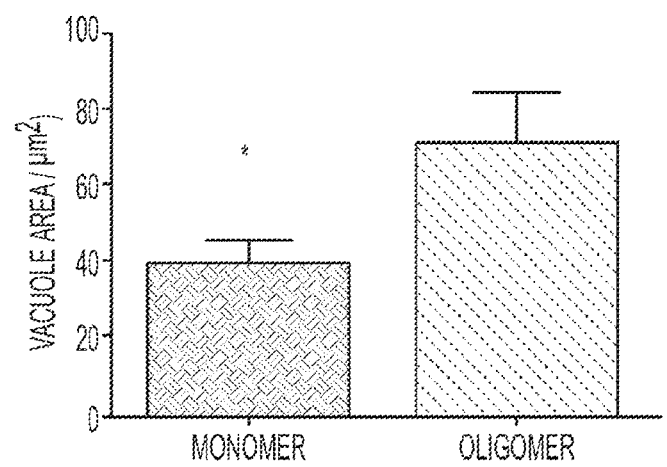
FIG. 8B. Graph of Vacuole Area ($\mu m^2$) measured with monomers or oligomers.
Figure 8C:
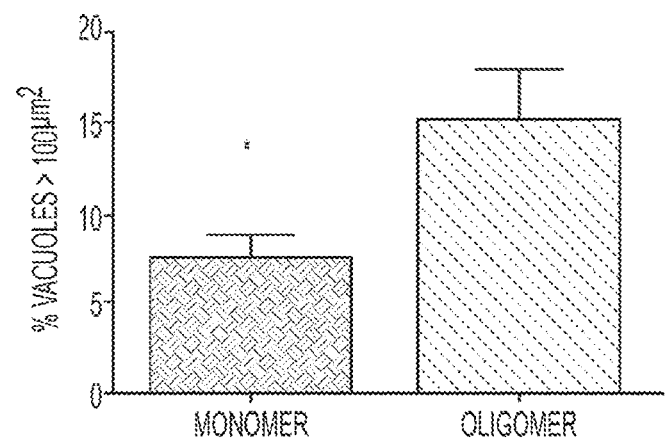
FIG. 8C. Graph of percent (%) Vacuoles >100 $\mu m^2$ measured with monomers or oligomers.
Figure 8D:
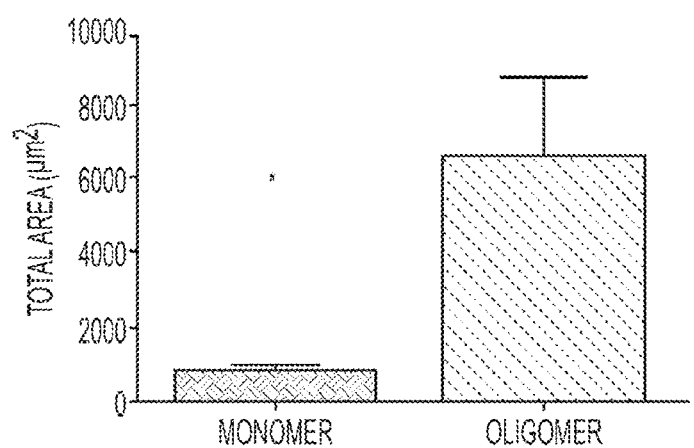
FIG. 8D. Graph of Total Area ($\mu m^2$) measured with monomers or oligomers.
Figure 9A:
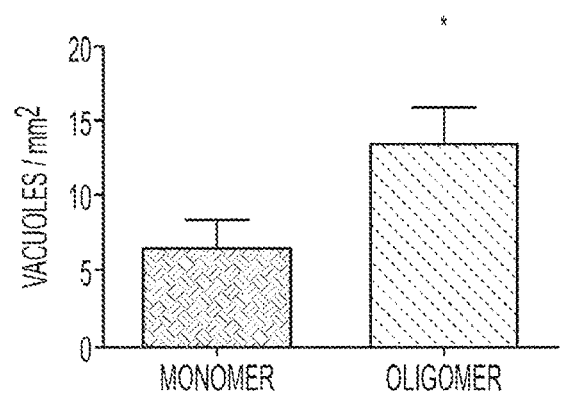
FIG. 9A. Graph of Vacuoles/$mm^2$ measured with monomers or oligomers.
Figure 9B:
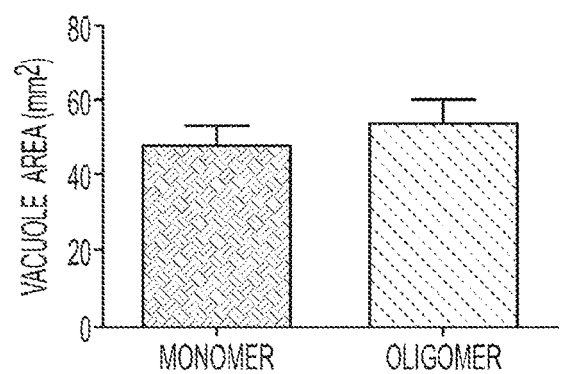
FIG. 9B. Graph of Vacuole Area ($\mu m^2$) measured with monomers or oligomers
Figure 9C:
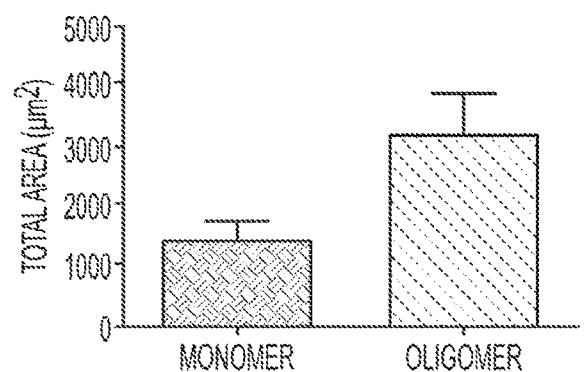
FIG. 9C. Graph of Total Area ($\mu m^2$) measured with monomers or oligomers.
Figure 9D:
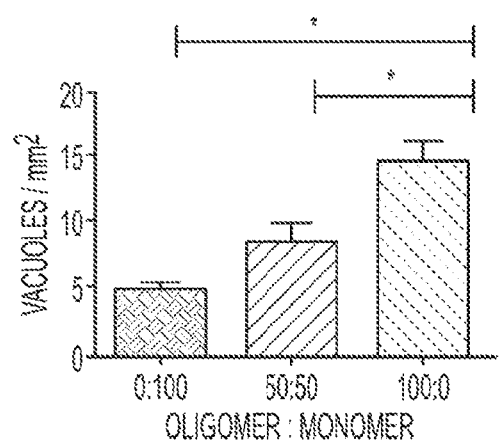
FIG. 9D. Graph of Vacuoles/$mm^2$ measured with monomers, monomers/oligomers, or oligomers.
Figure 9E:
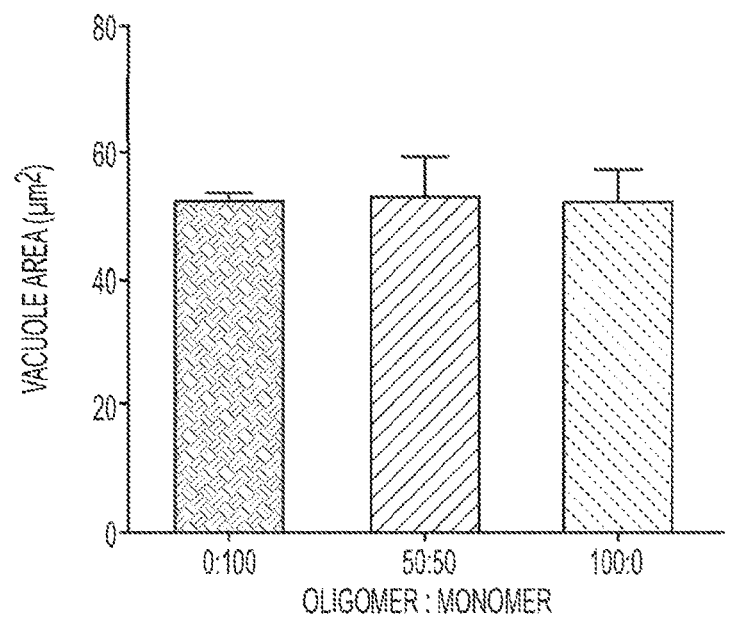
FIG. 9E Graph Vacuole Area ($\mu m^2$) measured with monomers, monomers/oligomers, or oligomers.
Figure 9F:
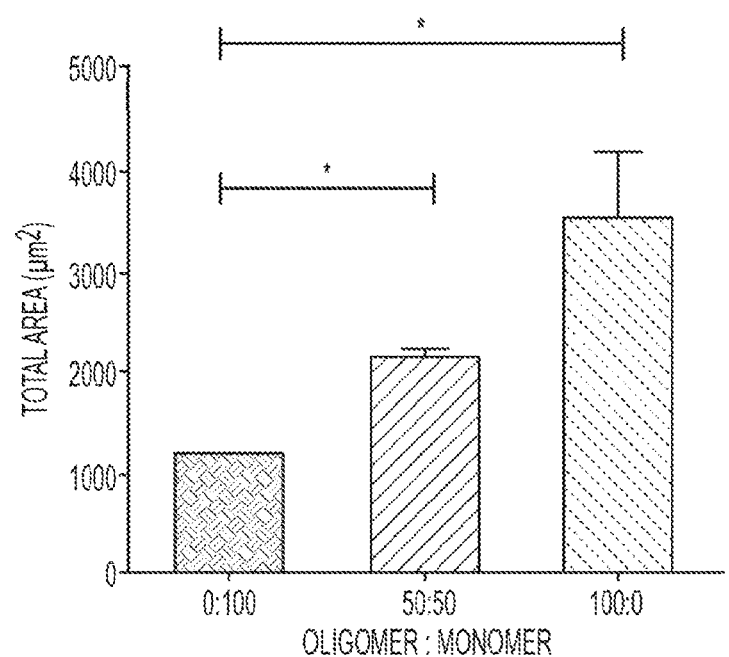
FIG. 9F. Graph of Total Area ($\mu m^2$) measured with monomers, monomers/oligomers, or oligomers.
Figure 10A:
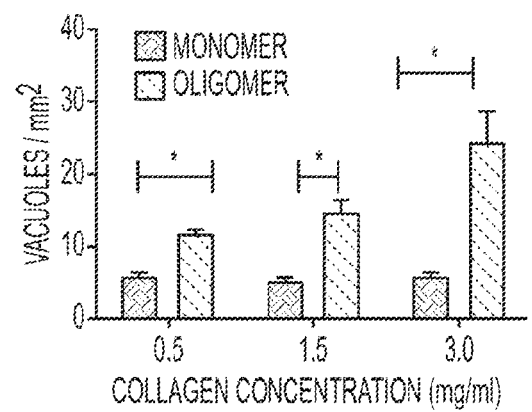
FIG. 10A. Graph of Vacuoles/$mm^2$ measured with monomers or oligomers at 3 concentrations of collagen (mg/ml).
Figure 10B:
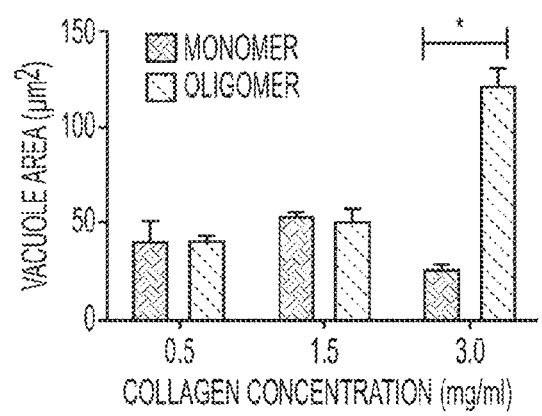
FIG. 10B. Graph of Vacuole Area ($\mu m^2$) measured with monomers or oligomers at 3 concentrations of collagen (mg/ml).
Figure 10C:
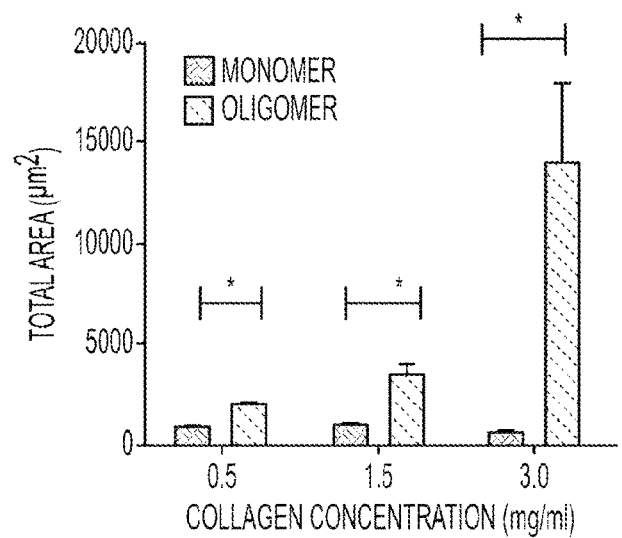
FIG. 10C. Graph of Total Area ($\mu m^2$) measured with monomers or oligomers at 3 concentrations of collagen (mg/ml).
Figure 10D:
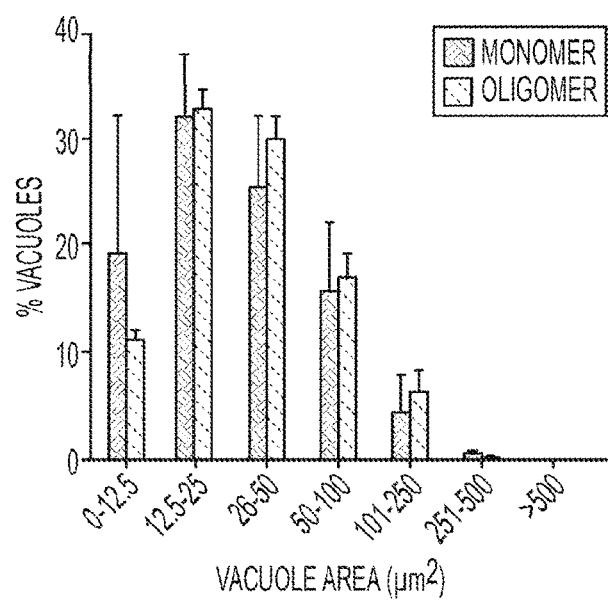
FIG. 10D. Graph of Percent (%) Vacuoles measured with monomers or oligomers at versus Vacuole Area ($\mu m^2$).
Figure 10E:
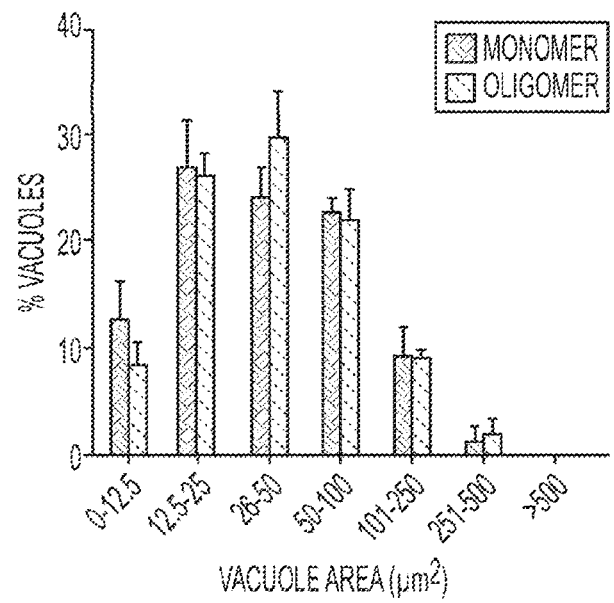
FIG. 10E. Graph Percent (%) Vacuoles measured with monomers, or oligomers versus Vacuole Area ($\mu m^2$).
Figure 10F:
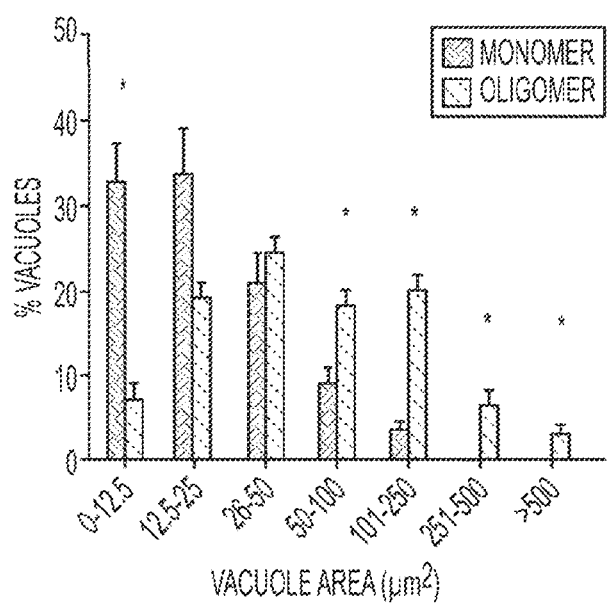
FIG. 10F. Graph Percent (%) Vacuoles measured with monomers, or oligomers versus Vacuole Area ($\mu m^2$).
Figure 11A:
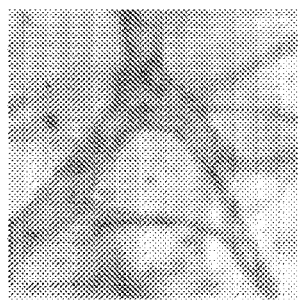
FIG. 11A. Photomicrograph of normal ECFC vacuole formation.
Figure 11B:
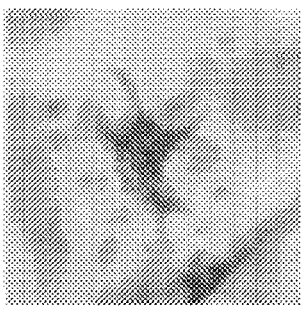
FIG. 11B. Photomicrograph of ECFC vacuole formation in the presence of the antibody MAB17781.
Figure 11C:
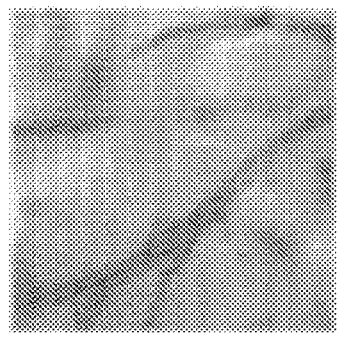
FIG. 11C. Photomicrograph of ECFC vacuole formation in the presence of Casin.
Figure 11D:
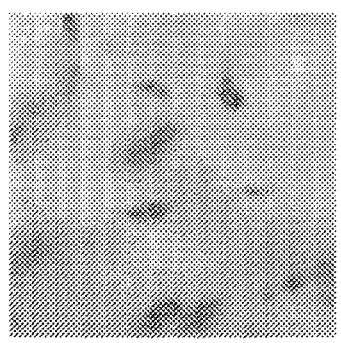
FIG. 11D. Photomicrograph of ECFC vacuole formation in the presence of the antibody NSC23766.
Figure 11E:
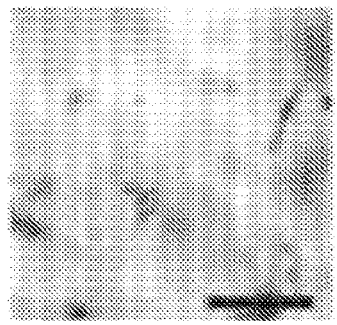
FIG. 11E. Photomicrograph of ECFC vacuole formation in the presence of TIMP-3.
Figure 11F:
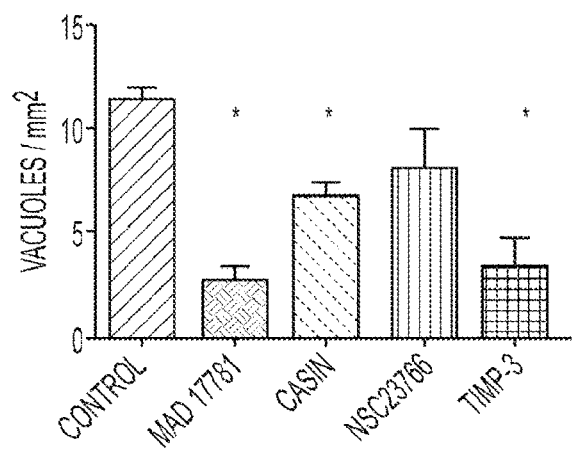
FIG. 11F. Graph of Vacuoles/($mm^2$) measured with ECFC control and cells exposed to MAB17781, Casin, NSC23766, or TIMP-3.
Figure 11G:
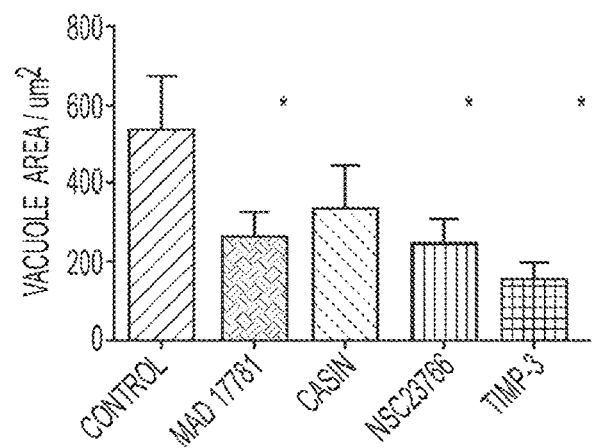
FIG. 11G. Graph of Vacuole Area ($\mu m^2$) measured with ECFC control and cells exposed to MAB17781, Casin, NSC23766, or TIMP-3.
Figure 11H:
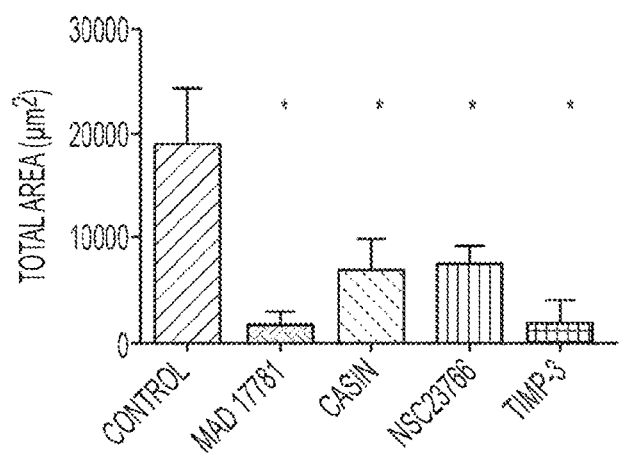
FIG. 11H. Graph of Total Area ($\mu m^2$) measured with ECFC control and cells exposed to MAB17781, Casin, NSC23766, or TIMP-3.

Referring now to FIG. 6, Panels A-F, ECFCs were able to form vacuoles in all matrices tested when seeded into the matrices at a density of about, 2×10⁶ cells/ml. However, the number and size of the vacuoles varied with the collagen concentration and cross link composition of the matrix. Previous reports from the literature have demonstrated an alteration in capillary morphogenesis with increasing matrix concentration in vitro and in vivo [74, 80, 122]. Consistent with these results collagen concentration altered ECFC vacuole formation.

TABLE 2

Primer sequences for qRTPCR.

| Name | Forward Primer | Reverse Primer |
| --- | --- | --- |
| ATP5B | CCACTACCAAGAAGGGATCTATCA (SEQ. ID NO. 1) | GGGCAGGGTCAGTCAAGTC (SEQ. ID NO. 2) |
| Cdc42 | CATCGGAATATGTACCGACTGTT (SEQ. ID NO. 3) | TGCAGTATCAAAAAGTCCAAGAGTA (SEQ. ID NO. 4) |
| MT1-MMP | CTGTCAGGAATGAGGATCTGAA (SEQ. ID NO. 5) | AGGGGTCACTGGAATGCTC (SEQ. ID NO. 6) |
| Rac1 | CTGATCAGTTACACAACCAATGC (SEQ. ID NO. 7) | CATTGGCAGAATAATTGTCAAAGA (SEQ. ID NO. 8) |

Referring now to FIGS. 9 A-C. ECFC Vacuole density and total vacuole area demonstrated a significant increase from 8.43±1.34 to 15.00±4.62 vacuoles/mm$^2$ and from 1519.34±312.66 to 7440.75±3431.11 μm$^2$ over the range of collagen concentrations tested, while vacuole area showed a trend of increasing with increasing collagen concentration from 40.07±5.88 to 73.94±21.48 μm2 (FIG. 7 A-D). The increase in vacuole area was due to a shift to right of the vacuole area distribution (FIG. 7C) and at the highest collagen concentration, vacuoles with an area greater than 500 μm$^2$ were found. The effect of cross link chemistry was also shown to have an effect on ECFC in vitro lumen formation.

Referring now to FIGS. 8 A-D. Matrices polymerized with the oligomer rich fraction demonstrated an increased vacuole density, vacuole area, and total vacuole area when compared to matrices polymerized with the monomer rich fraction. Vacuole density increased from 5.41±0.18 to 16.81±2.38, vacuoles/mm$^2$; vacuole area increased from 40.02±5.29 to 71.15±13.03, μm$^2$; and total vacuole area increased from 938.81±102.20 to 6612.60±2187.77, μm$^2$ in matrices polymerized from monomer and oligomer respectively. Additionally, there was a shift in the distribution of ECFC vacuole areas to the right in matrices polymerized from oligomer rich fractions compared to matrices polymerized from monomer rich fractions. Thus, both collagen concentration and collagen cross link chemistry alter ECFC vacuole formation in vitro.

Alteration in collagen cross link chemistry resulted in altered vacuolization in matrices with matched shear storage modulus (stiffness) but different collagen concentrations. Matrices were polymerized from both the oligomer and monomer rich fractions with a shear storage modulus of 200 Pa. Referring now to FIGS. 9 A-C, the matrices polymerized from the oligomer matrix demonstrated an increased vacuole density from 6.88±1.39 to 13.48±2.33 vacuoles/mm$^2$, and a trend of increased total vacuole area from 1455.69±210.37 to 3178.10±654.04 μm$^2$. The average vacuole area did not demonstrate a difference between the 200 Pa stiffness matrices polymerized from oligomer rich and monomer rich fractions. These data suggest that at a given stiffness the oligomer rich matrices are better able to support ECFC derived vacuoles. It is important to note that while these matrices have the same stiffness they have different collagen concentrations. The monomer rich matrix has a collagen concentration of 2.79 mg/ml and the oligomer rich matrix has a collagen concentration of 1.55 mg/ml. These data suggest that at a given stiffness a matrix with a reduced collagen concentration is better able to support ECFC vacuole formation.

Referring now to FIGS. 9 D-F. Vacuole density and total vacuole displayed an increase with increasing AMW (increasing ratio of collagen oligomers to collagen monomers) at a fixed collagen concentration of 1.5 mg/ml. To explore the role of the collagen cross link content in matrices with a fixed collagen concentration oligomer and monomer rich fractions were mixed to yield matrices with varied oligomer and monomer ratios. Matrices were polymerized with a collagen concentration of 1.5 mg/ml and a collagen oligomer to monomer ratio of 0:100, 50:50, and 100:0. Vacuole density demonstrated an increase from 5.04±0.20 to 14.75±1.58 vacuoles/mm$^2$ and total vacuole area increased from 1180.96±18.99 to 2090.31±51.72 μm$^2$ with increasing AMW, while average vacuole area did not demonstrate a significant difference with AMW ranging from 53.56±2.29 to 51.91±5.31 μm$^2$. These data further support the role for the collagen cross link chemistry as an important modulator of capillary morphogenesis.

Referring now to FIG. 6, ECFCs seeded into collagen based scaffolds undergo capillary morphogenesis. ECFCs seeded into matrices polymerized from oligomer rich fractions at 0.5 (FIG. 6 panel A), 1.5 (FIG. 6 panel B), and 3.0 (FIG. 6 panel C) mg/ml and monomer rich fractions at 0.5 (FIG. 6 panel D), 1.5 (FIG. 6 panel E), and 3.0 (FIG. 6 panel F) mg/ml formed vacuoles of different sizes and at different densities (scale bare=100 μm).

Referring now to FIGS. 7 A-C, collagen levels alter ECFC in vitro vacuole formation in collagen based scaffolds. ECFC vacuole density (FIG. 7A) and total vacuole area (FIG. 7D) significantly increased with increasing collagen concentration. Vacuole area (FIG. 7B) showed a trend of increasing with increasing collagen concentration due to a shift toward larger vacuole areas (FIG. 7C) (asterisk denotes $p<0.05$).

Referring now to FIGS. 10 A-C, matrices polymerized from oligomer rich fractions show an increase in vacuole density and total vacuole area over a range of collagen concentrations from 0.5 mg/ml to 3.0 mg/ml. Matrices were polymerized from either oligomer or monomer rich fractions at 0.5, 1.5, and 3.0 mg/ml. At each collagen concentration the matrix polymerized from the oligomer rich fraction demonstrated an increased vacuole density and total vacuole area. Additionally, at 3.0 mg/ml the matrix polymerized from the oligomer rich fraction displayed an increased average vacuole area compared to the matrix polymerized from the monomer rich fraction. The vacuole area distribution displayed a shift toward vacuoles of larger size for oligomer rich matrices with a collagen concentration of 3.0 mg/ml compared to 3.0 mg/ml matrices polymerized from monomer rich fraction (FIG. 10F). This alteration in vacuole area distribution with altered oligomer content is not seen at lower collagen concentrations.

Referring now to FIGS. 8 A-D, collagen matrices polymerized with oligomer and monomer rich fractions demonstrate altered ECFC in vitro vacuole formation. ECFCs displayed increased vacuole density (FIG. 8A), vacuole area (FIG. 8B), and total vacuole area (FIG. 8D) in matrices polymerized from oligomer rich fractions compared to those polymerized from monomeric rich fractions. The percentage of vacuoles with an area greater than 100 μm$^2$ was increased in the oligomer rich scaffolds (FIG. 8C, asterisk denotes $p<0.05$). Data represent Mean±SE and n=3.

Referring now to FIGS. 9 A-F, alterations in collagen cross link and AMW alter ECFC vacuole formation. Matrices polymerized from oligomer and monomer rich fraction with a stiffness of 200 Pa display differential ECFC vacuole formation (A-C). Matrices polymerized at 1.5 mg/ml with varied AMW demonstrate an increase in vacuole density and total vacuole area with increasing AMW (D-F, asterisk denotes $p<0.05$). Data represent Mean±SE and n=3.

Characterization of Matrix-Integrin-Cytoskeleton Signaling Axis in ECFC Vacuolization Capillary morphogenesis has been shown to be dependent upon signaling through β1 integrin to Rho GTPase family members Cdc42 and Rac1 [127] and to also depend on matrix remodeling by MT1-MMP [128]. To first determine if this signaling axis was involved in ECFC vacuole formation chemical inhibitors to β1 integrin, Cdc42, Rac1, and MT1-MMP were added to cultures to test if they would alter cell behavior.

Referring now to FIGS. 11 A-H, inhibition of the β1 integrin, Cdc42, Rac1, and MT1-MMP activity decreases ECFC total vascular area. Chemical inhibitors MAB17781, Casin, NSC23766 [129], and TIMP-3 were individually added to the cultures to inhibit β1 integrin, Cdc42, Rac1, and MT1-MMP activity respectively. While all inhibited ECFC vacuole formation, MAB17781 and TIMP-3 had the greatest reduction in vacuole density from 11.24±0.65 to 2.71±0.46 and 3.31±1.38 vacuoles/mm$^2$ respectively, vacuole area from 536.09±138.24 to 259.60±67.08 and 146.04±45.86 μm$^2$ respectively, and total vacuole area from 19103.60±5447.67 to 2387.82±620.56 an 2288.76±1685.92 μm$^2$ respectively. Additionally, inhibition of Cdc42 signaling decreased total vacuole area by decreasing vacuole density whereas inhibition of Rac1 signaling decreased total vacuole area by decreasing average vacuole area (FIGS. 11 G, H). These results suggest that while all of the proteins are involved in ECFC vacuole formation they play a nuanced role in the process.

Referring now to FIGS. 10 A-F, varied collagen cross link composition results in differential ECFC vacuole formation in vitro over a range of collagen concentrations. At 0.5, 1.5, and 3.0 mg/ml, matrices polymerized from oligomer rich fractions displayed an increase in vacuole density (FIG. 10A) and total vacuole area (FIG. 10C). At 3.0 mg/ml vacuole area was also significantly increased in oligomer rich scaffolds (FIG. 10B). This was due to a shift in the vacuole area distributions (FIGs. D-F, asterisk denotes p<0.05).

Figure 12A:
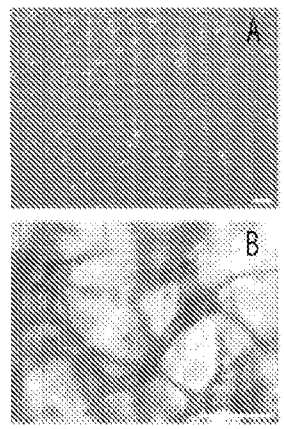
FIG. 12A. Photomicrograph of ECFC cultures grown on a tissue culture plastic (Panel A) or on collagen matrices (Panel B).

Alteration in mRNA expression by altered matrix microenvironment Culture of ECFCs in a 3D collagen matrix alters mRNA expression of Cdc42, Rac1, and MT1-MMP compared to ECFC grown in 2D culture. To begin to test for differences in cell signaling, mRNA was isolated from ECFCs grown on 2D tissue culture plastic and from ECFCs cultured in collagen matrices. The mRNA expression levels for Cdc42, Rac1, and MT1-MMP were normalized to ATP5B, a housekeeping gene for cells grown in 2D and 3D environments. Transcript levels were increased in ECFCs grown in a 3D environment compared to ECFCs cultured in a 2D environment for Cdc42 from 0.263±0.128 to 0.475±0.03, Rac1 from 0.374±0.069 to 0.840±0.093, and MT1-MMP from 0.012±0.001 to 0.308±0.033 (FIG. 12C). These data are not surprising given the differences in cell.

Referring now to FIGS. 11 A-H, alteration in signaling through the matrix integrin cytoskeleton axis disrupts ECFC in vitro vacuole formation. (A) control cultures displayed normal ECFC vacuole formation. The addition of MAB17781 (B), Casin (C), NSC23766 (D), or TIMP-3 (E, scale bare=100 μm) disrupt vacuole formation and lead to reductions in vacuole density (F), vacuole area (G), and total vacuole area (H, asterisk denotes p<0.05 compared to control cultures).

Figure 12B:
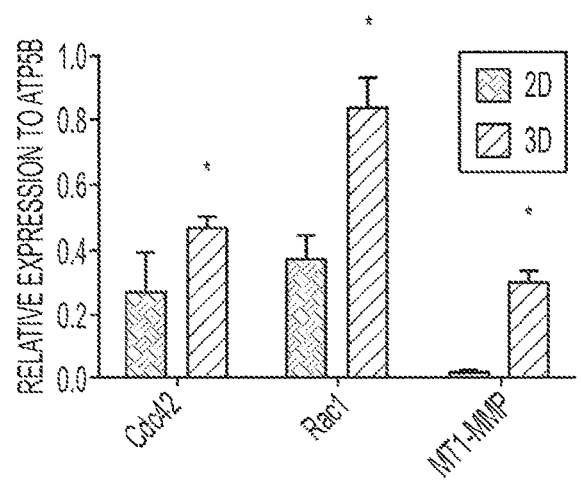
FIG. 12B. Graph of Relative Expression to ATP-5B measured for the following Cdc42, Rac1 and MT1-MMP.

Referring now to FIG. 12 A-B, culture of ECFCs in 3D collagen based scaffolds alters mRNA expression. Referring to FIG. 12 A, ECFCs displayed different morphology when grown on tissue culture plastic (FIG. 12 A, panel A, scale bar=100 μm) and in collagen matrices (FIG. 12 A, panel B, scale bar=100 μm) and exhibited altered expression of Cdc42, Rac1, and MT1-MMP mRNA (C, asterisk denotes p<0.05). Culture of ECFCs in 3D collagen based scaffolds alters mRNA expression. ECFCs displayed different morphology when grown on tissue culture plastic (FIG. 12 A, panel A, scale bar=100 μm) and in collagen matrices (FIG. 12 A, panel B, scale bar=100 μm) and exhibited altered expression of Cdc42, Rac1, and MT1-MMP mRNA (FIG. 12 B, asterisk denotes p<0.05). Data represent Mean±SE and n=3. morphology in the two different culture environments and further stresses the importance of investigating cell behavior in a 3D context which better recapitulates the in vivo environment. ECFCs seeded into matrices polymerized from oligomer rich fractions exhibit increased mRNA expression of Cdc42 and MT1-MMP and decreased expression of Rac1 compared to monomer rich fractions.

Next the mRNA expression from ECFCs cultured in matrices polymerized from both oligomer and monomer rich fractions at 0.5 and 3.0 mg/ml were compared. Referring now to FIGS. 13 A-C, collagen cross link chemistry alters ECFC mRNA expression. ECFC mRNA expression of Cdc42 (FIG. 13A), Rac1 (FIG. 13B), and MT1-MMP (FIG. 13C) in matrices polymerized with monomer or oligomer rich fractions at 0.5 and 3.0 mg/ml is altered. Matrices polymerized with oligomer rich collagen resulted in an up regulation of Cdc42 and MT1-MMP expression and a down regulation of Rac1 compared with monomer rich matrices (D, asterisk denotes p<0.05). While there was a trend of increased transcript levels for Cdc42 and MT1-MMP and decreased Rac1 mRNA expression in oligomer rich matrices at 0.5 and 3.0 mg/ml compared to monomer rich matrices at the same collagen concentration, the only significant difference was seen between 0.5 mg/ml oligomer rich and monomer rich matrices with expression levels of 0.571±0.022 and 0.393±0.054 respectively.

Figure 13A:
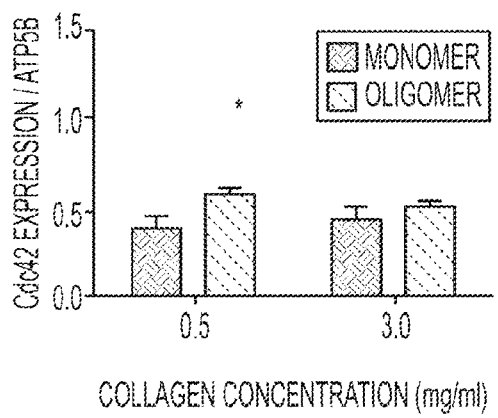
FIG. 13A. Graph of Cdc-42 Expression/ATP-5B Expression measured for either monomer or oligomer at both 0.5 and 30.0 mg/ml of Collagen.
Figure 13B:
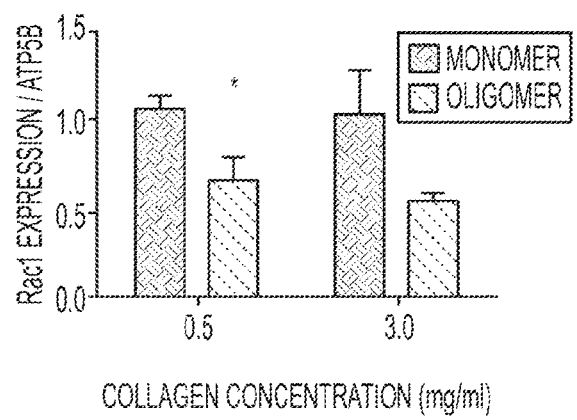
FIG. 13B. Graph of Rac1 Expression/ATP-5B Expression measured either with monomer or oligomer at both 0.5 and 30.0 mg/ml of Collagen.
Figure 13C:
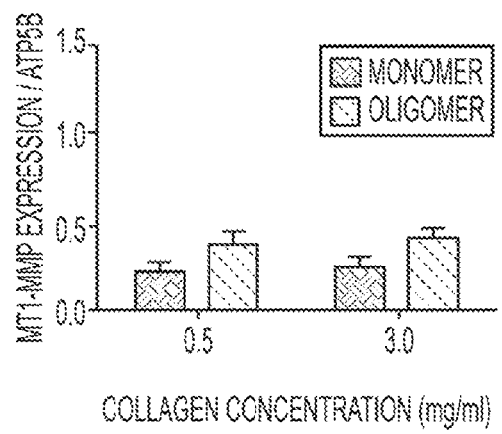
FIG. 13C. Graph of MT1-MMP Expression/ATP-5B Expression measured with either monomer or oligomer at both 0.5 and 30.0 mg/ml of Collagen.
Figure 13D:
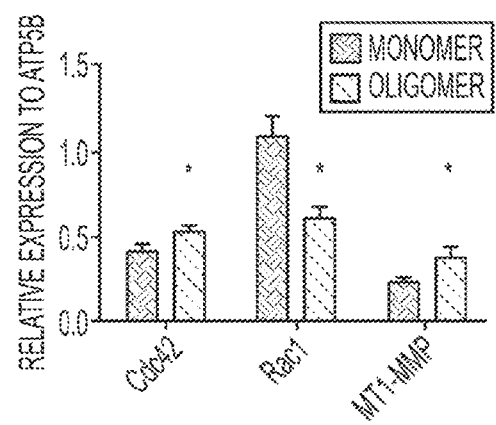
FIG. 13D. Graph of Relative Expression/ATP-5B Expression versus Cdc-42, Rac1 and MT1-MMP measured with either monomer or oligomer.

However, in comparing oligomer rich and monomer rich matrices, there were significant differences in mRNA expression in all three genes (FIG. 13D). Still referring to FIG. 13 D, the expression levels in oligomer and monomer matrices of Cdc42 mRNA was 0.535±0.021 and 0.415±0.039, the expression levels of Rac1 mRNA in oligomer and monomer matrices was 0.607±0.07 and 1.074±0.108, and the expression of MT1-MMP mRNA was 0.378±0.048 and 0.239±0.025 respectively. These data suggest that cross link chemistry plays a role in regulating ECFC mRNA expression during capillary morphogenesis. Alteration in Protein Expression by Altered Scaffold Biophysical Properties To determine if the varied microenvironment that the ECFCs experienced altered the protein expression level of ECFCs seeded into matrices polymerized of monomer and oligomer rich collagen, protein was isolated from ECFCs seeded into collagen matrices after 48 hours of culture. Endothelial cells interact with the collagen fibrils via integrin binding and activation leading to integrin clustering and focal adhesion formation. This outside in signaling is modulated by alterations in the biophysical properties of the matrix. To begin to interrogate alterations in the outside in signaling, focal adhesion kinase (FAK) protein expression was determined.

Figure 14:
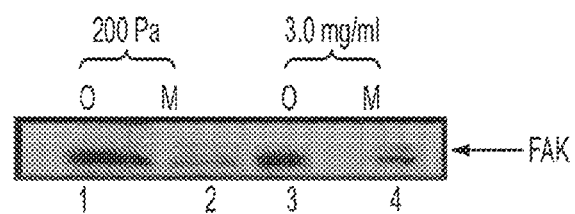
FIG. 14. Blot illustrating that FAK levels are elevated in ECFCs seeded into matrices polymerized from oligomer rich material.

Referring now to FIG. 14, FAK expression is elevated in ECFCs seeded into matrices polymerized from oligomer rich fractions compared to matrices polymerized from monomer rich fractions. ECFCs seeded into oligomer (O) or monomer (M) rich matrices at matched stiffness or collagen concentration display increased total FAK expression.

These data suggest that FAK protein expression is elevated in ECFCs seeded into matrices polymerized from oligomer rich fractions compared to ECFCs seeded into matrices polymerized from monomer rich fractions (FIG. 14). This elevation in FAK expression suggests increased outside in signaling into the endothelial cells which could be partially responsible for the increased vacuole formation in these oligomer rich matrices.

RhoGTPases are Present at Site of ECFC Vacuole Formation

Figure 15:
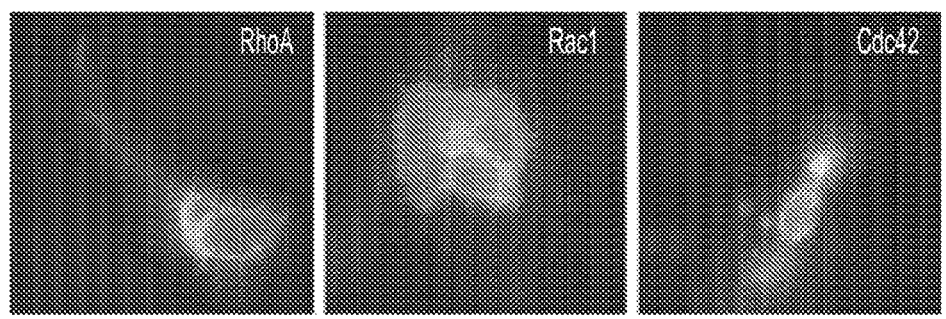
FIG. 15. Photomicrographs (magnified 400×) showing that the RhoGTPases: RhoA, Rac1, and Cdc42 are active in vacuole formation in ECFCs.

To begin to determine the alteration in RhoGTPase activity during capillary morphogenesis, ECFC were transfected with FRET based RhoA, Rac1, or Cdc42 plasmids and then seeded into oligomer rich matrices. Referring now to FIG. 15, RhoGTPases RhoA, Rac1, and Cdc42 are active at the site of vacuole formation in ECFCs (Images are at 400×). All three proteins appear to be active at the site of vacuole formation in ECFCs further suggesting they each may play a role in capillary morphogenesis.

Cell Density Alters ECFC Vacuole Formation in Collagen Matrices

Figure 16A:
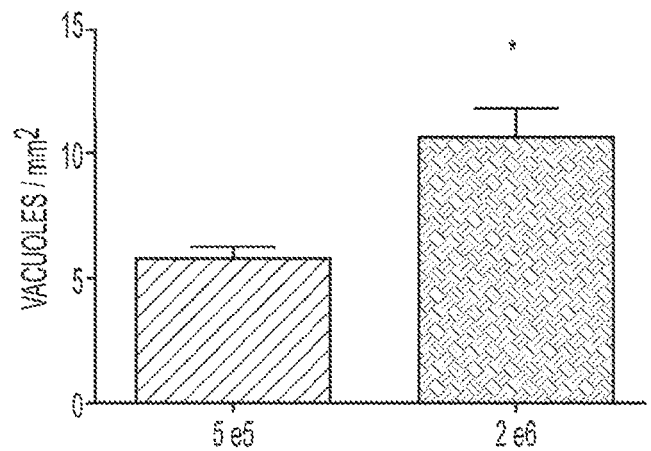
FIG. 16A. Graph of Vacuoles/$mm^2$ measured with either 5e 5 or 2 e 6 of ECFC cells.
Figure 16B:
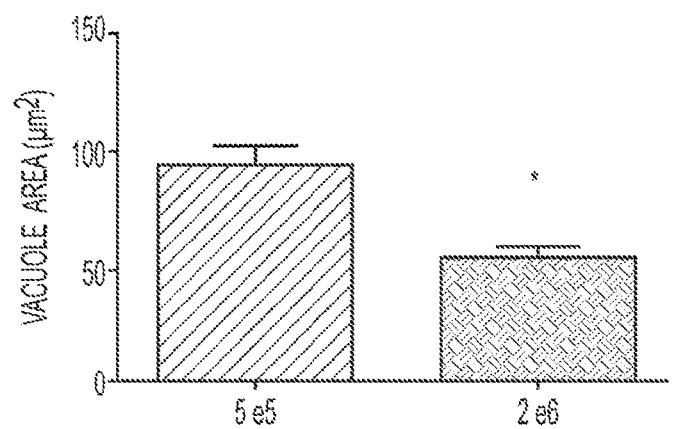
FIG. 16B. Graph of Vacuole Area ($\mu m^2$) measured with either 5e 5 or 2 e 6 of ECFC cells.
Figure 16C:
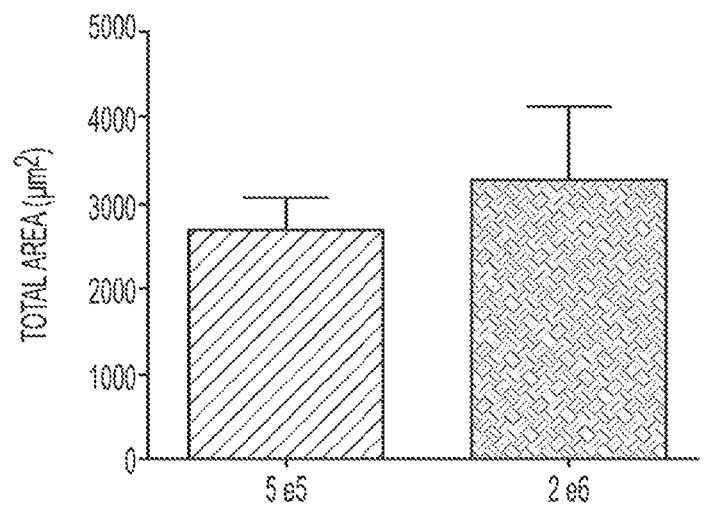
FIG. 16C. Graph of Total Area ($\mu m^2$) measured with either 5e 5 or 2 e 6 of ECFC cells.

The ratio of apparent matrix stiffness to cell traction has been demonstrated in the literature to impact capillary morphogenesis [74, 81]. In these previous reports when the ratio was too high capillary morphogenesis failed to occur, but when it was too low excessive contraction of the matrix resulted in cell death [74]. Referring now to FIGS. 16 A-C, ECFC density alters vacuole formation in collagen matrices. Increased cell seeding density results in increased vacuole density (FIG. 16A), but decreased vacuole area (FIG. 16B), and no change in total vacuole area (FIG. 16C, asterisk denotes p<0.05). To test for the effect of alterations in cell traction, the cell density of ECFCs seeded into the collagen based scaffolds was reduced from 2×106 cells/ml to 5×105 cells/ml. ECFCs seeded at a lower cell density demonstrated a lower vacuole density of 5.80±0.49 compared to 10.62±1.27 vacuoles/mm$^2$ at the higher cell seeding density (FIG. 16A), but an increased vacuole area of 94.90±8.43 compared to 54.08±5.27 μm$^2$ (FIG. 16B). Further the total vascular area was not significantly different between the two seeding densities.

Figure 17A:
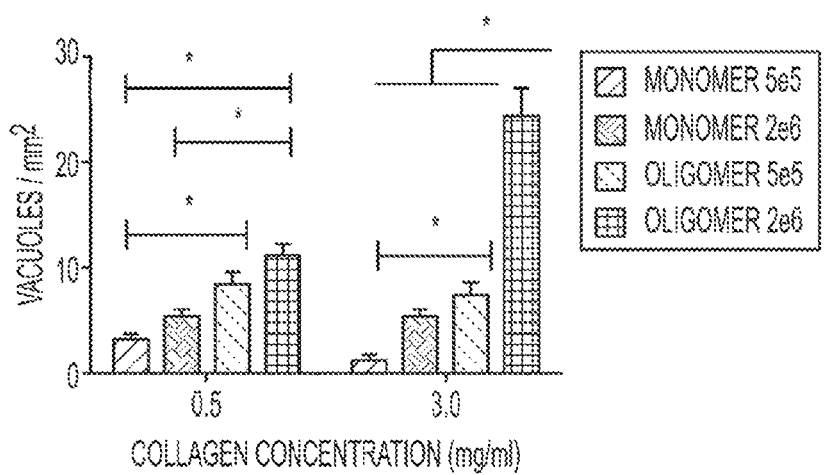
FIG. 17A. Graph of Vacuoles/$mm^2$ measured with 5c5 or 2e6 ECFC cells and either monomer or oligomer versus mg/ml of Collagen.
Figure 17B:
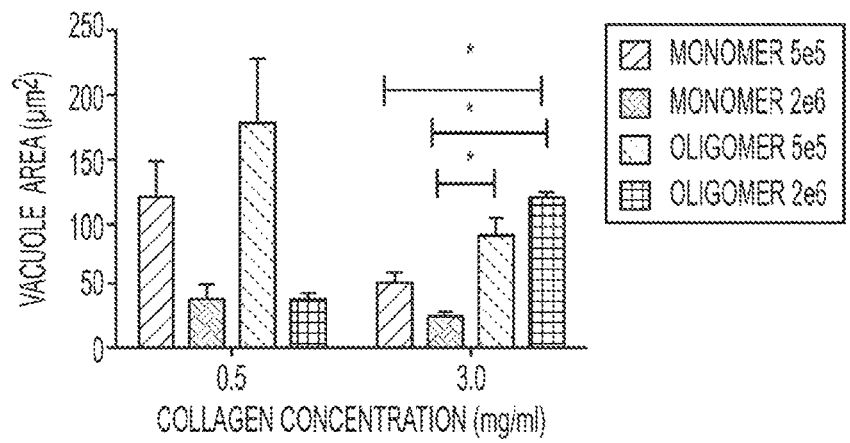
FIG. 17B. Graph of Vacuole Area ($\mu m^2$) measured with 5e5 or 2e6 ECFC cells and either monomer or oligomer versus mg/ml of Collagen.
Figure 17C:
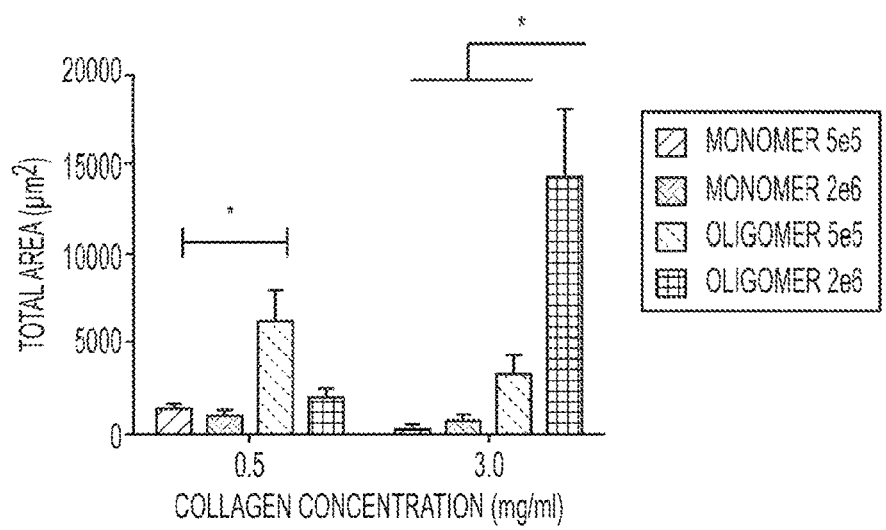
FIG. 17C. Graph of Total Area ($\mu m^2$) measured with 5e5 or 2e6 ECFC cells and either monomer or oligomer versus mg/ml of Collagen.

Matrices polymerized from oligomer and monomer rich fractions respond differently to alterations in cell seeding density. Matrices were polymerized from oligomer or monomer rich fractions with a collagen concentration of 0.5 and 3.0 mg/ml and seeded with either 5×10$^5$ or 2×10$^6$ cells/ml. Referring now to FIGS. 17 A-C, cell density alters ECFC in vitro vacuole formation. Increasing cell density resulted in increased vacuole density (FIG. 17A) for all matrices, but decreased vacuole area (FIG. 17B) and total vascular area (FIG. 17C) for all matrices except 3.0 mg/ml oligomer rich scaffolds (asterisk denotes p<0.05). As expected an increase in cell density resulted in an increase in vacuole density for each matrix (FIG. 17A). However the average vacuole area decreased with increasing cell density for all matrices except the oligomer rich matrix polymerized at 3 mg/ml (FIG. 17B). As a result total vacuole area decreased or remained unchanged with an increase in cell density for all matrices except for the 3.0 mg/ml oligomer matrix (FIG. 17C). This unexpected finding is due to a shift in the distribution of ECFC vacuoles toward smaller vacuole areas in the monomer rich and 0.5 mg/ml oligomer rich matrices (FIGS. 18 A-C). In contrast there is no leftward shift of the vacuole distribution in the 3.0 mg/ml oligomer rich scaffold and a trend of rightward shifting of vacuole size in this matrix. These data suggested the possibility that the ECFC generated traction and matrix remodeling could not be sufficiently resisted by the monomer rich and 0.5 mg/ml oligomer rich scaffolds.

Figure 18A:
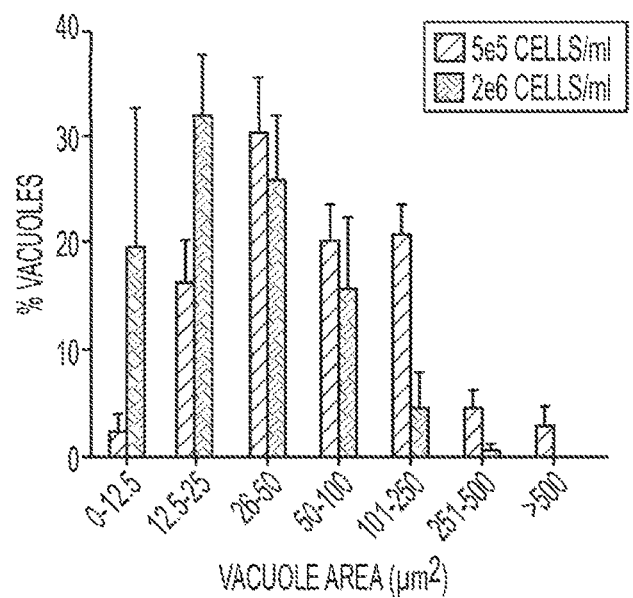
FIG. 18A. Graph of Percent (%) Vacuoles versus Vacuole Area ($\mu m^2$) measured with either 5e5 or 2e6 ECFC cells in monomer rich matrices and a Collagen Level of 0.5 mg/ml.
Figure 18B:
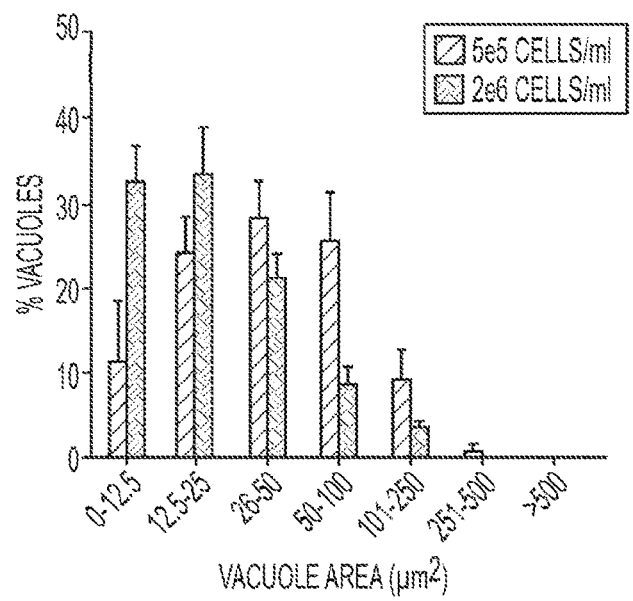
FIG. 18B. Graph of Percent (%) Vacuoles versus Vacuole Area ($\mu m^2$) measured with either 5e5 or 2e6 ECFC cells in monomer rich matrices and a Collagen Level of 3.0 mg/ml.
Figure 18C:
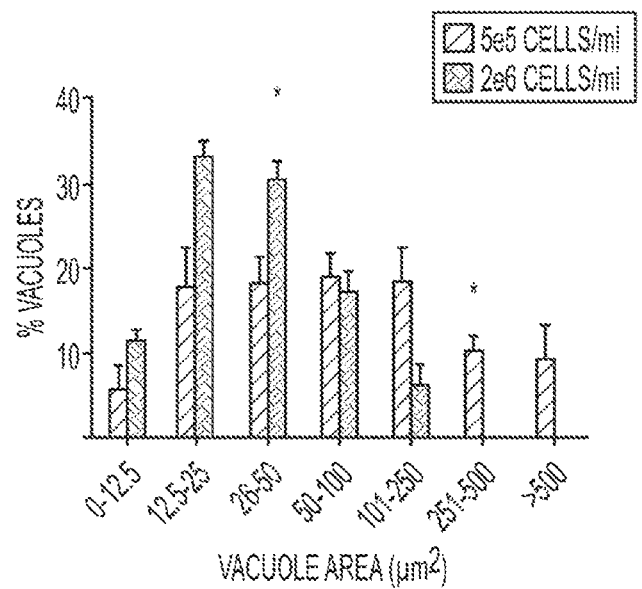
FIG. 18C. Graph of Percent (%) Vacuoles versus Vacuole Area ($\mu m^2$) measured with either 5e5 or 2e6 ECFC cells in oligomer rich matrices and a Collagen Level of 0.5 mg/ml.
Figure 18D:
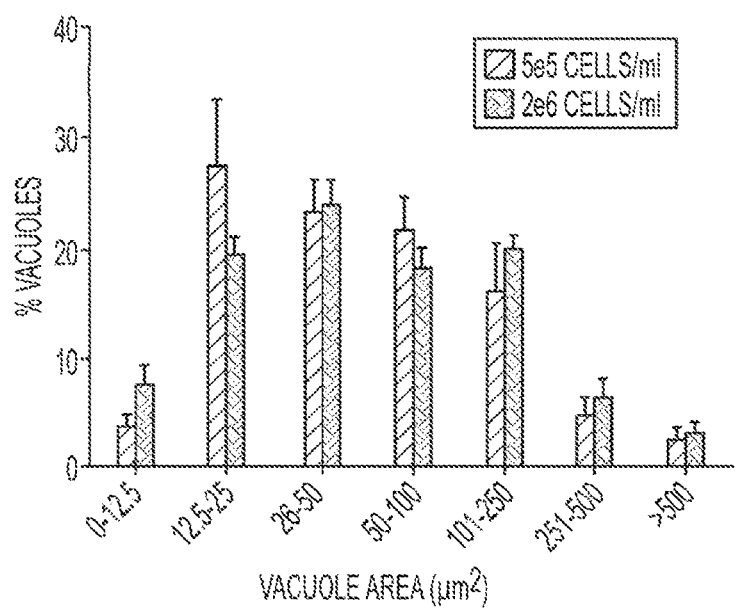
FIG. 18D. Graph of Percent (%) Vacuoles versus Vacuole Area ($\mu m^2$) measured with either 5e5 or 2e6 ECFC cells in oligomer rich matrices and a Collagen Level of 3.0 mg/ml.

Alterations in ECFC cell density result in varied vacuole area distributions. Referring now to FIGS. 18 A-D, the distribution of vacuole areas was shifted leftward for monomer rich matrices polymerized with a collagen concentration of 0.5 (FIG. 18A) and 3.0 (FIG. 18B) mg/ml and for oligomer rich matrices polymerized with a collagen concentration of 0.5 mg/ml (FIG. 18C). However this shift is not seen in oligomer rich matrices polymerized at a collagen concentration of 3.0 mg/ml (FIG. 18D).

For the purposes of promoting an understanding of the principles of the novel technology, reference will now be made to the preferred embodiments thereof, and specific language will be used to describe the same. It will nevertheless be understood that no limitation of the scope of the novel technology is thereby intended, such alterations, modifications, and further applications of the principles of the novel technology being contemplated as would normally occur to one skilled in the art to which the novel technology relates are within the scope of this disclosure and the claims.

REFERENCES

1. Bailey, J. L., P. J. Critser, C. Whittington, J. L. Kuske, M. C. Yoder, and S. L. Voytik-Harbin, Collagen oligomers modulate physical and biological properties of three-dimensional self-assembled matrices. Biopolymers, 2011. 95(2): p. 77-93.
2. Adams, R. H. and K. Alitalo, Molecular regulation of angiogenesis and lymphangiogenesis. Nat Rev Mol Cell Biol, 2007. 8(6): p. 464-478.
3. Conway, E. M., D. Collen, and P. Carmeliet, Molecular mechanisms of blood vessel growth. Cardiovasc Res, 2001. 49(3): p. 507-521.
4. Carmeliet, P. and R. K. Jain, Angiogenesis in cancer and other diseases. Nature, 2000. 407(6801): p. 249-257.
5. Jain, R. K., P. Au, J. Tam, D. G. Duda, and D. Fukumura, Engineering vascularized tissue. Nat Biotechnol, 2005. 23(7): p. 821-823.
6. Kawamoto, A. and T. Asahara, Role of progenitor endothelial cells in cardiovascular disease and upcoming therapies. Catheter Cardiovasc Interv, 2007. 70(4): p. 477-484.
7. Levenberg, S., Engineering blood vessels from stem cells: recent advances and applications. Current Opinion in Biotechnology, 2005. 16(5): p. 516-523.
8. Yoder, M. C., L. E. Mead, D. Prater, T. R. Krier, K. N. Mroueh, F. Li, R. Krasich, C. J. Temm, J. T. Prchal, and D. A. Ingram, Redefining endothelial progenitor cells via clonal analysis and hematopoietic stem/progenitor cell principals. Blood, 2007. 109(5): p. 1801-1809.
9. Au, P., L. M. Daheron, D. G. Duda, K. S. Cohen, J. A. Tyrrell, R. M. Lanning, D. Fukumura, D. T. Scadden, and R. K. Jain, Differential in vivo potential of endothelial progenitor cells from human umbilical cord blood and adult peripheral blood to form functional long-lasting vessels. Blood, 2008. 111(3): p. 1302-1305.
10. Melero-Martin, J. M., Z. A. Khan, A. Picard, X. Wu, S. Paruchuri, and J. Bischoff, In vivo vasculogenic potential of human blood-derived endothelial progenitor cells. Blood, 2007. 109(11): p. 4761-4768.
11. Schechner, J. S., A. K. Nath, L. Zheng, M. S. Kluger, C. C. Hughes, M. R. Sierra-Honigmann, M. I. Lorber, G. Tellides, M. Kashgarian, A. L. Bothwell, and J. S. Pober, In vivo formation of complex microvessels lined by human endothelial cells in an immunodeficient mouse. Proc Natl Acad Sci USA, 2000. 97(16): p. 9191-9196.
12. Shepherd, B. R., D. R. Enis, F. Wang, Y. Suarez, J. S. Pober, and J. S. Schechner, Vascularization and engraftment of a human skin substitute using circulating progenitor cell-derived endothelial cells. FASEB J, 2006. 20(10): p. 1739-1741.
13. Ng, C. P., C. L. Helm, and M. A. Swartz, Interstitial flow differentially stimulates blood and lymphatic endothelial cell morphogenesis in vitro. Microvasc Res, 2004. 68(3): p. 258-264.
14. Luong, E. and S. Gerecht, Stem cells and scaffolds for vascularizing engineered tissue constructs. Adv Biochem Eng Biotechnol, 2009. 114: p. 129-172.

15. Koike, N., D. Fukumura, O. Gralla, P. Au, J. S. Schechner, and R. K. Jain, Tissue engineering: creation of long-lasting blood vessels. Nature, 2004. 428(6979): p. 138-139.
16. Lesman, A., M. Habib, O. Caspi, A. Gepstein, G. Arbel, S. Levenberg, and L. Gepstein, Transplantation of a tissue-engineered human vascularized cardiac muscle. Tissue Eng Part A. 16(1): p. 115-125.
17. Asahara, T., T. Murohara, A. Sullivan, M. Silver, R. van der Zee, T. Li, B. Witzenbichler, G. Schatteman, and J. M. Isner, Isolation of putative progenitor endothelial cells for angiogenesis. Science, 1997. 275(5302): p. 964-967.
18. Vasa, M., S. Fichtlscherer, A. Aicher, K. Adler, C. Urbich, H. Martin, A. M. Zeiher, and S. Dimmeler, Number and Migratory Activity of Circulating Endothelial Progenitor Cells Inversely Correlate With Risk Factors for Coronary Artery Disease. Circ Res, 2001. 89(1): p. e 1-7.
19. Hill, J. M., G. Zalos, J. P. J. Halcox, W. H. Schenke, M. A. Waclawiw, A. A. Quyyumi, and T. Finkel, Circulating Endothelial Progenitor Cells, Vascular Function, and Cardiovascular Risk. N Engl J Med, 2003. 348(7): p. 593-600.
20. Schatteman, G. C., M. Dunnwald, and C. Jiao, Biology of bone marrow-derived endothelial cell precursors. Am J Physiol Heart Circ Physiol, 2007. 292(1): p. H1-18.
21. Prater, D. N., J. Case, D. A. Ingram, and M. C. Yoder, Working hypothesis to redefine endothelial progenitor cells. Leukemia, 2007. 21(6): p. 1141-1149.
22. Lin, Y., D. J. Weisdorf, A. Solovey, and R. P. Hebbel, Origins of circulating endothelial cells and endothelial outgrowth from blood. J Clin Invest, 2000. 105(1): p. 71-77.
23. Ingram, D. A., L. E. Mead, H. Tanaka, V. Meade, A. Fenoglio, K. Mortell, K. Pollok, M. J. Ferkowicz, D. Gilley, and M. C. Yoder, Identification of a novel hierarchy of endothelial progenitor cells using human peripheral and umbilical cord blood. Blood, 2004. 104(9): p. 2752-2760.
24. Peichev, M., A. J. Naiyer, D. Pereira, Z. Zhu, W. J. Lane, M. Williams, M. C. Oz, D. J. Hicklin, L. Witte, M. A. S. Moore, and S. Rafii, Expression of VEGFR-2 and AC133 by circulating human CD34+ cells identifies a population of functional endothelial precursors. Blood, 2000. 95(3): p. 952-958.
25. Risau, W. and I. Flamme, Vasculogenesis. Annu Rev Cell Dev Biol, 1995. 11: p. 73-91.
26. Hirschi, K. K., D. A. Ingram, and M. C. Yoder, Assessing Identity, Phenotype, and Fate of Endothelial Progenitor Cells. Arterioscler Thromb Vasc Biol, 2008. 28(9): p. 1584-1595.
27. Vasa, M., S. Fichtlscherer, K. Adler, A. Aicher, H. Martin, A. M. Zeiher, and S. Dimmeler, Increase in Circulating Endothelial Progenitor Cells by Statin Therapy in Patients With Stable Coronary Artery Disease. Circulation, 2001. 103(24): p. 2885-2890.
28. Rehman, J., J. Li, C. M. Orschell, and K. L. March, Peripheral Blood "Endothelial Progenitor Cells" Are Derived From Monocyte/Macrophages and Secrete Angiogenic Growth Factors. Circulation, 2003. 107(8): p. 1164-1169.
29. Kalka, C., H. Masuda, T. Takahashi, W. M. Kalka-Moll, M. Silver, M. Kearney, T. Li, J. M. Isner, and T. Asahara, Transplantation of ex vivo expanded endothelial progenitor cells for therapeutic neovascularization. Proceedings of the National Academy of Sciences, 2000. 97(7): p. 3422-3427.
30. Asosingh, K., M. A. Aldred, A. Vasanji, J. Drazba, J. Sharp, C. Farver, S. A. A. Comhair, W. Xu, L. Licina, L. Huang, B. Anand-Apte, M. C. Yoder, R. M. Tuder, and S. C. Erzurum, Circulating Angiogenic Precursors in Idiopathic Pulmonary Arterial Hypertension. Am J Pathol, 2008. 172(3): p. 615-627.
31. Hur, J., C.-H. Yoon, H.-S. Kim, J.-H. Choi, H.-J. Kang, K.-K. Hwang, B.-H. Oh, M.-M. Lee, and Y.-B. Park, Characterization of Two Types of Endothelial Progenitor Cells and Their Different Contributions to Neovasculogenesis. Arterioscler Thromb Vasc Biol, 2004. 24(2): p. 288-293.
32. Hanjaya-Putra, D., V. Bose, Y.-I. Shen, J. Yee, S. Khetan, K. Fox-Talbot, C. Steenbergen, J. A. Burdick, and S. Gerecht, Controlled activation of morphogenesis to generate a functional human microvasculature in a synthetic matrix. Blood, 2011.
33. Stratman, A. N., K. M. Malotte, R. D. Mahan, M. J. Davis, and G. E. Davis, Pericyte recruitment during vasculogenic tube assembly stimulates endothelial basement membrane matrix formation. Blood, 2009. 114(24): p. 5091-5101.
34. Gerecht-Nir, S., A. Ziskind, S. Cohen, and J. Itskovitz-Eldor, Human embryonic stem cells as an in vitro model for human vascular development and the induction of vascular differentiation. Lab Invest, 2003. 83(12): p. 1811-1820.
35. Wang, Z. Z., P. Au, T. Chen, Y. Shao, L. M. Daheron, H. Bai, M. Arzigian, D. Fukumura, R. K. Jain, and D. T. Scadden, Endothelial cells derived from human embryonic stem cells form durable blood vessels in vivo. Nat Biotech, 2007. 25(3): p. 317-318.
36. Ferreira, L. S., S. Gerecht, H. F. Shieh, N. Watson, M. A. Rupnick, S. M. Dallabrida, G. Vunjak-Novakovic, and R. Langer, Vascular progenitor cells isolated from human embryonic stem cells give rise to endothelial and smooth muscle like cells and form vascular networks in vivo. Circ Res, 2007. 101(3): p. 286-294.
37. Lees, J. G., S. A. Lim, T. Croll, G. Williams, S. Lui, J. Cooper-White, L. R. McQuade, B. Mathiyalagan, and B. E. Tuch, Transplantation of 3D scaffolds seeded with human embryonic stem cells: biological features of surrogate tissue and teratoma-forming potential. Regen Med, 2007. 2(3): p. 289-300.
38. Park, I. H., N. Arora, H. Huo, N. Maherali, T. Ahfeldt, A. Shimamura, M. W. Lensch, C. Cowan, K. Hochedlinger, and G. Q. Daley, Disease-specific induced pluripotent stem cells. Cell, 2008. 134(5): p. 877-886.
39. Ebert, A. D., J. Yu, F. F. Rose, Jr., V. B. Mattis, C. L. Lorson, J. A. Thomson, and C. N. Svendsen, Induced pluripotent stem cells from a spinal muscular atrophy patient. Nature, 2009. 457(7227): p. 277-280.
40. Tateishi, K., J. He, O. Taranova, G. Liang, A. C. D'Alessio, and Y. Zhang, Generation of insulin-secreting islet-like clusters from human skin fibroblasts. J Biol Chem, 2008. 283(46): p. 31601-31607.
41. Maehr, R., S. Chen, M. Snitow, T. Ludwig, L. Yagasaki, R. Goland, R. L. Leibel, and D. A. Melton, Generation of pluripotent stem cells from patients with type 1 diabetes. Proc Natl Acad Sci USA, 2009. 106(37): p. 15768-15773.
42. Choi, K. D., J. Yu, K. Smuga-Otto, G. Salvagiotto, W. Rehrauer, M. Vodyanik, J. Thomson, and I. Slukvin, Hematopoietic and endothelial differentiation of human induced pluripotent stem cells. Stem Cells, 2009. 27(3): p. 559-567.

43. Taura, D., M. Sone, K. Homma, N. Oyamada, K. Takahashi, N. Tamura, S. Yamanaka, and K. Nakao, Induction and isolation of vascular cells from human induced pluripotent stem cells—brief report. Arterioscler Thromb Vasc Biol, 2009. 29(7): p. 1100-1103.

44. Pedersen, J. A. and M. A. Swartz, Mechanobiology in the third dimension. Ann Biomed Eng, 2005. 33(11): p. 1469-1490.

45. Sieminski, A. L., A. S. Was, G. Kim, H. Gong, and R. D. Kamm, The stiffness of three-dimensional ionic self-assembling peptide gels affects the extent of capillary-like network formation. Cell Biochem Biophys, 2007. 49(2): p. 73-83.

46. Hanjaya-Putra, D., J. Yee, D. Ceci, R. Truitt, D. Yee, and S. Gerecht, Vascular endothelial growth factor and substrate mechanics regulate in vitro tubulogenesis of endothelial progenitor cells. J Cell Mol Med, 2009.

47. Silva, E. A., E.-S. Kim, H. J. Kong, and D. J. Mooney, Material-based deployment enhances efficacy of endothelial progenitor cells. Proceedings of the National Academy of Sciences, 2008. 105(38): p. 14347-14352.

48. Zeugolis, D. I., R. G. Paul, and G. Attenburrow, Factors influencing the properties of reconstituted collagen fibers prior to self-assembly: Animal species and collagen extraction method. Journal of Biomedical Materials Research Part A, 2008. 86A(4): p. 892-904.

49. Kreger, S. T. and S. L. Voytik-Harbin, Hyaluronan concentration within a 3D collagen matrix modulates matrix viscoelasticity, but not fibroblast response. Matrix Biol, 2009. 28(6): p. 336-346.

50. Zeugolis, D. I., Gordon R. Paul Geoffrey Attenburrow, Cross-linking of extruded collagen fibers—A biomimetic three-dimensional scaffold for tissue engineering applications. Journal of Biomedical Materials Research Part A, 2008. 9999(9999): p. NA.

51. Guidry, C. and F. Grinnell, Studies on the mechanism of hydrated collagen gel reorganization by human skin fibroblasts. J Cell Sci, 1985. 79(1): p. 67-81.

52. Guidry, C., Contraction of Hydrated Collagen Gels by Fibroblasts: Evidence for Two Mechanisms by which Collagen Fibrils are Stabilized. Collagen Rel. Res., 1986. 6: p. 515-529.

53. Wang, N., J. P. Butler, and D. E. Ingber, Mechanotransduction Across the Cell Surface and Through the Cytoskeleton. Science, 1993. 260(5111): p. 1124-1127.

54. Rupp, P. A. and C. D. Little, Integrins in Vascular Development. Circ Res, 2001. 89(7): p. 566-572.

55. Galbraith, C. G. and M. P. Sheetz, Forces on adhesive contacts affect cell function. Current Opinion in Cell Biology, 1998. 10(5): p. 566-571.

56. Ingber, D., In search of cellular control: Signal transduction in context. Journal of Cellular Biochemistry, 1998. 72(S30-31): p. 232-237.

57. Chen, C. S., M. Mrksich, S. Huang, G. M. Whitesides, and D. E. Ingber, Geometric Control of Cell Life and Death. Science, 1997. 276(5317): p. 1425-1428.

58. McBeath, R., D. M. Pirone, C. M. Nelson, K. Bhadriraju, and C. S. Chen, Cell shape, cytoskeletal tension, and RhoA regulate stem cell lineage commitment. Dev Cell, 2004. 6(4): p. 483-495.

59. Ruiz, S. A. and C. S. Chen, Emergence of Patterned Stem Cell Differentiation within Multicellular Structures. Stem Cells, 2008: p. 2008-0432.

60. Engler, A. J., S. Sen, H. L. Sweeney, and D. E. Discher, Matrix Elasticity Directs Stem Cell Lineage Specification. Cell, 2006. 126(4): p. 677-689.

61. Folkman, J. and C. Haudenschild, Angiogenesis in vitro. Nature, 1980. 288(5791): p. 551-556.

62. Vernon, R. B. and E. H. Sage, Between molecules and morphology. Extracellular matrix and creation of vascular form. Am J Pathol, 1995. 147(4): p. 873-883.

63. Ingber, D. E., J. A. Madri, and J. Folkman, Endothelial growth factors and extracellular matrix regulate DNA synthesis through modulation of cell and nuclear expansion. In vitro Cell Dev Biol, 1987. 23(5): p. 387-394.

64. Montesano, R., J. D. Vassalli, A. Baird, R. Guillemin, and L. Orci, Basic Fibroblast Growth Factor Induces Angiogenesis in vitro. Proceedings of the National Academy of Sciences, 1986. 83(19): p. 7297-7301.

65. Ingber, D. E. and J. Folkman, Mechanochemical switching between growth and differentiation during fibroblast growth factor-stimulated angiogenesis in vitro: role of extracellular matrix. J Cell Biol, 1989. 109(1): p. 317-330.

66. Davis, G. E. and C. W. Camarillo, An [alpha]2[beta]1 Integrin-Dependent Pinocytic Mechanism Involving Intracellular Vacuole Formation and Coalescence Regulates Capillary Lumen and Tube Formation in Three-Dimensional Collagen Matrix. Experimental Cell Research, 1996. 224(1): p. 39-51.

67. Kanzawa, S., H. Endo, and N. Shioya, Improved in vitro angiogenesis model by collagen density reduction and the use of type III collagen. Ann Plast Surg, 1993. 30(3): p. 244-251.

68. Ment, L., W. Stewart, D. Scaramuzzino, and J. Madri, An in vitro three-dimensional coculture model of cerebral microvascular angiogenesis and differentiation. In vitro Cellular & Developmental Biology—Animal, 1997. 33(9): p. 684-691.

69. Ilan, N., S. Mahooti, and J. A. Madri, Distinct signal transduction pathways are utilized during the tube formation and survival phases of in vitro angiogenesis. J Cell Sci, 1998. 111(24): p. 3621-3631.

70. Korff, T. and H. G. Augustin, Tensional forces in fibrillar extracellular matrices control directional capillary sprouting. J Cell Sci, 1999. 112 (Pt 19): p. 3249-3258.

71. Salazar, R., S. E. Bell, and G. E. Davis, Coordinate Induction of the Actin Cytoskeletal Regulatory Proteins Gelsolin, Vasodilator-Stimulated Phosphoprotein, and Profilin during Capillary Morphogenesisin vitro. Experimental Cell Research, 1999. 249(1): p. 22-32.

72. Vernon, R. B. and E. H. Sage, A Novel, Quantitative Model for Study of Endothelial Cell Migration and Sprout Formation within Three-Dimensional Collagen Matrices. Microvascular Research, 1999. 57(2): p. 118-133.

73. Yang, S., J. Graham, J. W. Kahn, E. A. Schwartz, and M. E. Gerritsen, Functional Roles for PECAM-1 (CD31) and VE-Cadherin (CD144) in Tube Assembly and Lumen Formation in Three-Dimensional Collagen Gels. Am J Pathol, 1999. 155(3): p. 887-895.

74. Sieminski, A. L., R. P. Hebbel, and K. J. Gooch, The relative magnitudes of endothelial force generation and matrix stiffness modulate capillary morphogenesis in vitro. Exp Cell Res, 2004. 297(2): p. 574-584.

75. Koh, W., R. D. Mahan, and G. E. Davis, Cdc42- and Rac1-mediated endothelial lumen formation requires Pak2, Pak4 and Par3, and PKC-dependent signaling. J Cell Sci, 2008. 121(Pt 7): p. 989-1001.

76. Matsumura, T., K. Wolff, and P. Petzelbauer, Endothelial cell tube formation depends on cadherin 5 and CD31 interactions with filamentous actin. J Immunol, 1997. 158(7): p. 3408-3416.

77. Stratman, A. N., W. B. Saunders, A. Sacharidou, W. Koh, K. E. Fisher, D. C. Zawieja, M. J. Davis, and G. E. Davis, Endothelial cell lumen and vascular guidance tunnel formation requires MT1-MMP-dependent proteolysis in 3-dimensional collagen matrices. Blood, 2009. 114(2): p. 237-247.

78. Melero-Martin, J. M., M. E. De Obaldia, S. Y. Kang, Z. A. Khan, L. Yuan, P. Oettgen, and J. Bischoff, Engineering robust and functional vascular networks in vivo with human adult and cord blood-derived progenitor cells. Circ Res, 2008. 103(2): p. 194-202.

79. Au, P., J. Tam, D. Fukumura, and R. K. Jain, Bone marrow-derived mesenchymal stem cells facilitate engineering of long-lasting functional vasculature. Blood, 2008. 111(9): p. 4551-4558.

80. Ghajar, C. M., X. Chen, J. W. Harris, V. Suresh, C. C. W. Hughes, N. L. Jeon, A. J. Putnam, and S. C. George, The Effect of Matrix Density on the Regulation of 3-D Capillary Morphogenesis. Biophysical Journal, 2008. 94(5): p. 1930-1941.

81. Kniazeva, E. and A. J. Putnam, Endothelial cell traction and ECM density influence both capillary morphogenesis and maintenance in 3-D. American Journal of Physiology—Cell Physiology, 2009. 297(1): p. C179-C187.

82. Karman, R. Y., H. J. Salacinski, K. Sales, P. Butler, and A. M. Seifalian, The roles of tissue engineering and vascularisation in the development of micro-vascular networks: a review. Biomaterials, 2005. 26(14): p. 1857-1875.

83. Asahara, T., H. Masuda, T. Takahashi, C. Kalka, C. Pastore, M. Silver, M. Kearne, M. Magner, and J. M. Isner, Bone marrow origin of endothelial progenitor cells responsible for postnatal vasculogenesis in physiological and pathological neovascularization. Circ Res, 1999. 85(3): p. 221-228.

84. Mund, J. A., D. A. Ingram, M. C. Yoder, and J. Case, Endothelial progenitor cells and cardiovascular cell-based therapies. Cytotherapy, 2009. 11(2): p. 103-113.

85. Chavakis, E., A. Aicher, C. Heeschen, K. Sasaki, R. Kaiser, N. El Makhfi, C. Urbich, T. Peters, K. Scharffetter-Kochanek, A. M. Zeiher, T. Chavakis, and S. Dimmeler, Role of beta2-integrins for homing and neovascularization capacity of endothelial progenitor cells. J Exp Med, 2005. 201(1): p. 63-72.

86. Jiang, M., B. Wang, C. Wang, B. He, H. Fan, T. B. Guo, Q. Shao, L. Gao, and Y. Liu, Angiogenesis by transplantation of HIF-1 alpha modified EPCs into ischemic limbs. J Cell Biochem, 2008. 103(1): p. 321-334.

87. Suuronen, E. J., J. P. Veinot, S. Wong, V. Kapila, J. Price, M. Griffith, T. G. Mesana, and M. Ruel, Tissue-engineered injectable collagen-based matrices for improved cell delivery and vascularization of ischemic tissue using CD133+ progenitors expanded from the peripheral blood. Circulation, 2006. 114(1): p. 1138-144.

88. Ingram, D. A., L. E. Mead, D. B. Moore, W. Woodard, A. Fenoglio, and M. C. Yoder, Vessel wall-derived endothelial cells rapidly proliferate because they contain a complete hierarchy of endothelial progenitor cells. Blood, 2005. 105(7): p. 2783-2786.

89. Bell, S. E., A. Mavila, R. Salazar, K. J. Bayless, S. Kanagala, S. A. Maxwell, and G. E. Davis, Differential gene expression during capillary morphogenesis in 3D collagen matrices: regulated expression of genes involved in basement membrane matrix assembly, cell cycle progression, cellular differentiation and G-protein signaling. J Cell Sci, 2001. 114(15): p. 2755-2773.

90. Davis, G. E., K. J. Bayless, and A. Mavila, Molecular basis of endothelial cell morphogenesis in three-dimensional extracellular matrices. Anat Rec, 2002. 268(3): p. 252-275.

91. Davis, G. E. and W. B. Saunders, Molecular balance of capillary tube formation versus regression in wound repair: role of matrix metalloproteinases and their inhibitors. J Investig Dermatol Symp Proc, 2006. 11(1): p. 44-56.

92. Hynes, R. O., B. L. Bader, and K. Hodivala-Dilke, Integrins in vascular development. Braz J Med Biol Res, 1999. 32(5): p. 501-510.

93. Stupack, D. G. and D. A. Cheresh, ECM remodeling regulates angiogenesis: endothelial integrins look for new ligands. Sci STKE, 2002. 119: p. pe7.

94. Krishnan, L., C. J. Underwood, S. Maas, B. J. Ellis, T. C. Kode, J. B. Hoying, and J. A. Weiss, Effect of mechanical boundary conditions on orientation of angiogenic microvessels. Cardiovasc Res, 2008. 78(2): p. 324-332.

95. Vailhe, B., D. Vittet, and J. J. Feige, In vitro models of vasculogenesis and angiogenesis. Lab Invest, 2001. 81(4): p. 439-452.

96. Ghajar, C. M., X. Chen, J. W. Harris, V. Suresh, C. C. W. Hughes, N. L. Jeon, A. J. Putnam, and S. C. George, The effect of matrix density on the regulation of 3-D capillary morphogenesis. Biophys J, 2008. 94(5): p. 1930-1941.

97. Ruegg, C. and A. Mariotti, Vascular integrins: pleiotropic adhesion and signaling molecules in vascular homeostasis and angiogenesis. Cell Mol Life Sci, 2003. 60(6): p. 1135-1157.

98. Larsen, M., V. V. Artym, J. A. Green, and K. M. Yamada, The matrix reorganized: extracellular matrix remodeling and integrin signaling. Curr Opin Cell Biol, 2006. 18(5): p. 463-471.

99. Yamamura, N., R. Sudo, M. Ikeda, and K. Tanishita, Effects of the mechanical properties of collagen gel on the in vitro formation of microvessel networks by endothelial cells. Tissue Eng, 2007. 13(7): p. 1443-1453.

100. Enis, D. R., B. R. Shepherd, Y. Wang, A. Qasim, C. M. Shanahan, P. L. Weissberg, M. Kashgarian, J. S. Pober, and J. S. Schechner, Induction, differentiation, and remodeling of blood vessels after transplantation of Bcl-2-transduced endothelial cells. Proceedings of the National Academy of Sciences of the United States of America, 2005. 102(2): p. 425-430.

101. Voytik-Harbin, S. L., Three-dimensional extracellular matrix substrates for cell culture. Methods Cell Biol, 2001. 63: p. 561-581.

102. March, K. L. and B. H. Johnstone, Cellular approaches to tissue repair in cardiovascular disease: the more we know, the more there is to learn. Am J Physiol Heart Circ Physiol, 2004. 287(2): p. H458-463.

103. Ghosh, K. and D. E. Ingber, Micromechanical control of cell and tissue development: implications for tissue engineering. Adv Drug Deliv Rev, 2007. 59(13): p. 1306-1318.

104. Meredith, J. E., Jr. and M. A. Schwartz, Integrins, adhesion and apoptosis. Trends Cell Biol, 1997. 7(4): p. 146-150.

105. Assoian, R. K. and M. A. Schwartz, Coordinate signaling by integrins and receptor tyrosine kinases in the regulation of G1 phase cell-cycle progression. Curr Opin Genet Dev, 2001. 11(1): p. 48-53.

106. Senger, D. R., C. A. Perruzzi, M. Streit, V. E. Kotcliansky, A. R. de Fougerolles, and M. Detmar, The alpha(1) beta(1) and alpha(2)beta(1) integrins provide critical support for vascular endothelial growth factor signaling, 107. Mammoto, A. and D. E. Ingber, Cytoskeletal control of growth and cell fate switching. Curr Opin Cell Biol, 2009.
108. Roeder, B. A., K. Kokini, J. E. Sturgis, J. P. Robinson, and S. L. Voytik-Harbin, Tensile mechanical properties of three-dimensional type I collagen extracellular matrices with varied microstructure. J Biomech Eng, 2002. 124(2): p. 214-222.
109. Kreger, S. T., B. J. Bell, J. Bailey, E. Stites, J. Kuske, B. Waisner, and S. L. Voytik-Harbin, Polymerization and matrix physical properties as important design considerations for soluble collagen formulations. Biopolymers, 2010. 93(8): p. 690-707.
110. Miller, E. J. and R. K. Rhodes, Preparation and characterization of the different types of collagen. Methods Enzymol, 1982. 82 Pt A: p. 33-64.
111. Marquez, J. P., G. M. Genin, K. M. Pryse, and E. L. Elson, Cellular and matrix contributions to tissue construct stiffness increase with cellular concentration. Ann Biomed Eng, 2006. 34(9): p. 1475-1482.
112. Wiedeman, M. P., Dimensions of blood vessels from distributing artery to collecting vein. Circ Res, 1963. 12: p. 375-378.
113. Abraham, L. C., E. Zuena, B. Perez-Ramirez, and D. L. Kaplan, Guide to collagen characterization for biomaterial studies. Journal of Biomedical Materials Research Part B: Applied Biomaterials, 2008. 87B(1): p. 264-285.
114. Even-Ram, S. and K. M. Yamada, Cell migration in 3D matrix. Curr Opin Cell Biol, 2005. 17(5): p. 524-532.
115. Sabeh, F., R. Shimizu-Hirota, and S. J. Weiss, Protease-dependent versus -independent cancer cell invasion programs: three-dimensional amoeboid movement revisited. J Cell Biol, 2009. 185(1): p. 11-19.
116. Johnson, K. R., J. L. Leight, and V. M. Weaver, Demystifying the effects of a three-dimensional microenvironment in tissue morphogenesis. Methods Cell Biol, 2007. 83: p. 547-583.
117. Ingber, D., Mechanical signaling. Ann N Y Acad Sci, 2002. 961: p. 162-163.
118. Jain, R. K., Molecular regulation of vessel maturation. Nat Med, 2003. 9(6): p. 685-693.
119. Iruela-Arispe, M. L. and G. E. Davis, Cellular and molecular mechanisms of vascular lumen formation. Dev Cell, 2009. 16(2): p. 222-231.
120. Sacharidou, A., W. Koh, A. N. Stratman, A. M. Mayo, K. E. Fisher, and G. E. Davis, Endothelial lumen signaling complexes control 3D matrix-specific tubulogenesis through interdependent Cdc42- and MT1-MMP-mediated events. Blood: p. blood-2009-2011-252692. 121. Kniazeva, E., S. Kachgal, and A. J. Putnam, Effects of extracellular matrix density and mesenchymal stem cells on neovascularization in vivo. Tissue Eng Part A, 2011. 17(7-8): p. 905-914.
122. Critser, P. J., S. T. Kreger, S. L. Voytik-Harbin, and M. C. Yoder, Collagen matrix physical properties modulate endothelial colony forming cell derived vessels in vivo. Microvasc Res.
123. Mammoto, A., K. M. Connor, T. Mammoto, C. W. Yung, D. Huh, C. M. Aderman, G. Mostoslaysky, L. E. Smith, and D. E. Ingber, A mechanosensitive transcriptional mechanism that controls angiogenesis. Nature, 2009. 457(7233): p. 1103-1108.
124. Eyre, D. R., M. A. Paz, and P. M. Gallop, Cross-Linking in Collagen and Elastin. Annual Review of Biochemistry, 1984. 53(1): p. 717-748.
125. Cronlund, A. L., B. D. Smith, and H. M. Kagan, Binding of Lysyl Oxidase to Fibrils of Type I Collagen. Connective Tissue Research, 1985. 14(2): p. 109-119.
126. Koh, W., A. N. Stratman, A. Sacharidou, and G. E. Davis, Chapter 5 In vitro Three Dimensional Collagen Matrix Models of Endothelial Lumen Formation During Vasculogenesis and Angiogenesis, in Methods in Enzymology. 2008, Academic Press. p. 83-101.
127. Bayless, K. J. and G. E. Davis, The Cdc42 and Rac1 GTPases are required for capillary lumen formation in three-dimensional extracellular matrices. J Cell Sci, 2002. 115(6): p. 1123-1136.
128. Sacharidou, A., W. Koh, A. N. Stratman, A. M. Mayo, K. E. Fisher, and G. E. Davis, Endothelial lumen signaling complexes control 3D matrix-specific tubulogenesis through interdependent Cdc42- and MT1-MMP-mediated events. Blood, 2010. 115(25): p. 5259-5269.
129. Gao, Y., J. B. Dickerson, F. Guo, J. Zheng, and Y. Zheng, Rational design and characterization of a Rac GTPase-specific small molecule inhibitor. Proceedings of the National Academy of Sciences of the United States of America, 2004. 101(20): p. 7618-7623.
130. Sieminski, A. L., R. P. Hebbel, and K. J. Gooch, Improved microvascular network in vitro by human blood outgrowth endothelial cells relative to vessel-derived endothelial cells. Tissue Eng, 2005. 11(9-10): p. 1332-1345.
131. Sander, E. A. and V. H. Barocas, Biomimetic Collagen Tissues: Collagenous Tissue Engineering and Other Applications, in Collagen, P. Fratzl, Editor. 2008, Springer US. p. 475-504.
132. Davis, G. E. and D. R. Senger, Endothelial extracellular matrix: biosynthesis, remodeling, and functions during vascular morphogenesis and neovessel stabilization. Circ Res, 2005. 97(11): p. 1093-1107.
133. Tan, W., T. R. Palmby, J. Gavard, P. Amornphimoltham, Y. Zheng, and J. S. Gutkind, An essential role for Rac1 in endothelial cell function and vascular development. The FASEB Journal, 2008. 22(6): p. 1829-1838.
134. Hu, Y. L., S. Li, H. Miao, T. C. Tsou, M. A. del Pozo, and S. Chien, Roles of Microtubule Dynamics and Small GTPase Rac in Endothelial Cell Migration and Lamellipodium Formation under Flow. Journal of Vascular Research, 2002. 39(6): p. 465-476.
135. Koh, W., K. Sachidanandam, A. N. Stratman, A. Sacharidou, A. M. Mayo, E. A. Murphy, D. A. Cheresh, and G. E. Davis, Formation of endothelial lumens requires a coordinated PKCepsilon-, Src-, Pak- and Raf-kinase-dependent signaling cascade downstream of Cdc42 activation. J Cell Sci, 2009. 122(Pt 11): p. 1812-1822.
136. Plopper, G., H. McNamee, L. Dike, K. Bojanowski, and D. Ingber, Convergence of integrin and growth factor receptor signaling pathways within the focal adhesion complex. Mol. Biol. Cell, 1995. 6(10): p. 1349-1365.
137. Romer, L. H., K. G. Birukov, and J. G. N. Garcia, Focal Adhesions: Paradigm for a Signaling *Nexus*. Circ Res, 2006. 98(5): p. 606-616. 138. [cited 2007; Available from: HTTP://DIABETES.NIDDK.NIH.GOV.
139. Stevens Dennis, L., Chapter 119. Infections of the Skin, Muscle, and Soft Tissues, in Harrison's Principles of Internal Medicine, B. E. Fauci A S, Kasper D L, Hauser S L, Longo D L, Jameson J L, Loscalzo J, Editor.
140. Huang, P., S. Li, M. Han, Z. Xiao, R. Yang, and Z. C. Han, Autologous transplantation of granulocyte colony-stimulating factor-mobilized peripheral blood mononu- 141. Minamino, T., H. Toko, K. Tateno, T. Nagai, and I. Komuro, Peripheral-blood or bone-marrow mononuclear cells for therapeutic angiogenesis? Lancet, 2002. 360 (9350): p. 2083-2084; author reply 2084.
142. Suh, W., K. L. Kim, J. M. Kim, I. S. Shin, Y. S. Lee, J. Y. Lee, H. S. Jang, J. S. Lee, J. Byun, J. H. Choi, E. S. Jeon, and D. K. Kim, Transplantation of endothelial progenitor cells accelerates dermal wound healing with increased recruitment of monocytes/macrophages and neovascularization. Stem Cells, 2005. 23(10): p. 1571-1578.
143. Traktuev, D. O., S. Merfeld-Clauss, J. Li, M. Kolonin, W. Arap, R. Pasqualini, B. H. Johnstone, and K. L. March, A population of multipotent CD34-positive adipose stromal cells share pericyte and mesenchymal surface markers, reside in a periendothelial location, and stabilize endothelial networks. Circ Res, 2008. 102(1): p. 77-85.
144. Covas, D. T., R. A. Panepucci, A. M. Fontes, W. A. Silva, Jr., M. D. Oreliana, Freitas, L. Neder, A. R. Santos, L. C. Peres, M. C. Jamur, and M. A. Zago, Multipotent mesenchymal stromal cells obtained from diverse human tissues share functional properties and gene-expression profile with CD146+ perivascular cells and fibroblasts. Exp Hematol, 2008. 36(5): 642-654.
145. Kogler, G., S. Sensken, J. A. Airey, T. Trapp, M. Muschen, N. Feldhahn, S. Liedtke, R. V. Sorg, J. Fischer, C. Rosenbaum, S. Greschat, A. Knipper, J. Bender, O. Degistirici, J. Gao, A. I. Caplan, E. J. Colletti, G. Almeida-Porada, H. W. Muller, E. Zanjani, and P. Wernet, A new human somatic stem cell from placental cord blood with intrinsic pluripotent differentiation potential. J Exp Med, 2004. 200(2): p. 123-135.
146. Kogler, G., S. Sensken, and P. Wernet, Comparative generation and characterization of pluripotent unrestricted somatic stem cells with mesenchymal stem cells from human cord blood. Exp Hematol, 2006. 34(11): p. 1589-1595.
147. Deshane, J., S. Chen, S. Caballero, A. Grochot-Przeczek, H. Was, S. Li Calzi, R. Lach, T. D. Hock, B. Chen, N. Hill-Kapturczak, G. P. Siegal, J. Dulak, A. Jozkowicz, M. B. Grant, and A. Agarwal, Stromal cell-derived factor 1 promotes angiogenesis via a heme oxygenase 1-dependent mechanism. J Exp Med, 2007. 204(3): p. 605-618.
148. Kung, E. F., F. Wang, and J. S. Schechner, In vivo perfusion of human skin substitutes with microvessels formed by adult circulating endothelial progenitor cells. Dermatol Surg, 2008. 34(2): p. 137-146.
149. Davidson, J. M., Animal models for wound repair. Archives of Dermatological Research, 1998. 290(14): p.
150. Galiano, R. D., J.t. Michaels, M. Dobryansky, J. P. Levine, and G. C. Gurtner, Quantitative and reproducible murine model of excisional wound healing. Wound Repair Regen, 2004. 12(4): p. 485-492.
151. Ito, H., I. I. Rovira, M. L. Bloom, K. Takeda, V. J. Ferrans, A. A. Quyyumi, and T. Finkel, Endothelial Progenitor Cells as Putative Targets for Angiostatin. Cancer Res, 1999. 59(23): p. 5875-5877.
152. Sieveking, D. P., A. Buckle, D. S. Celermajer, and M. K. C. Ng, Strikingly Different Angiogenic Properties of Endothelial Progenitor Cell Subpopulations: Insights From a Novel Human Angiogenesis Assay. Journal of the American College of Cardiology, 2008. 51(6): p. 660-668.
153. Ziegelhoeffer, T., B. Fernandez, S. Kostin, M. Heil, R. Voswinckel, A. Helisch, and W. Schaper, Bone Marrow-Derived Cells Do Not Incorporate Into the Adult Growing Vasculature. Circ Res, 2004. 94(2): p. 230-238.
154. Wood, G. C. and M. K. Keech, The formation of fibrils from collagen solutions. 1. The effect of experimental conditions: kinetic and electron-microscope studies. Biochem J, 1960. 75: p. 588-598.

We claim:

1. A vessel forming composition comprising a population of endothelial colony forming cells (ECFCs) cultured in a polymerized acid soluble Type I collagen matrix derived from pig skin collagen having a ratio of collagen oligomers to collagen monomers between 100:0 and 50:50.

2. The vessel forming composition of claim 1, wherein the polymerized acid soluble Type I collagen matrix has a ratio of collagen oligomers to collagen monomers of 50:50.

3. The vessel forming composition of claim 1, wherein the matrix has a collagen concentration of about 0.5 to about 3.0 mg/ml.

4. The vessel forming composition of claim 1, wherein the shear storage modulus or stiffness of the matrix is at least two fold greater than a polymerized acid soluble Type I collagen matrix derived from pig skin having a ratio of collagen oligomers to collagen monomers of 0:100.

5. The vessel forming composition of claim 1, wherein the endothelial colony forming cells (ECFCs) cultured in the polymerized acid soluble Type I collagen matrix having a ratio of collagen oligomers to collagen monomers of 100:0 produce an at least three fold higher number of vacuoles/mm$^2$ relative to endothelial colony forming cells (ECFCs) cultured in a polymerized acid soluble Type I collagen matrix derived from pig skin having a ratio of collagen oligomers to collagen monomers of 0:100.

6. The vessel forming composition of claim 1, wherein the expression of Cdc42, FAK and Membrane Type I-matrix metalloproteinase (MT1-MMP) genes in endothelial colony forming cells (ECFCs) cultured in a polymerized acid soluble Type I collagen matrix having a ratio of collagen oligomers to collagen monomers of 100:0 is increased relative to the corresponding gene expression in endothelial colony forming cells (ECFCs) cultured in a polymerized acid soluble Type I collagen matrix derived from pig skin having a ratio of collagen oligomers to collagen monomers of 0:100.

7. The vessel forming composition of claim 1, wherein Rac1 gene expression in endothelial colony forming cells (ECFCs) cultured in the polymerized matrix having a ratio of collagen oligomers to collagen monomers of 100:0 is reduced relative to Rac1 gene expression in endothelial colony forming cells (ECFCs) cultured in a polymerized matrix having a ratio of collagen oligomers to collagen monomers of 0:100.

8. A method for producing capillary morphogenesis in a collagen matrix comprising culturing a population of endothelial colony forming cells (ECFCs) in a polymerized Type I acid soluble collagen matrix derived from pig skin having a ratio of collagen oligomers to collagen monomers of between 100:0 and 50:50, wherein capillaries are formed.

9. The method of claim 8, wherein the polymerized matrix of Type I acid soluble collagen has a collagen concentration of about 0.5 to about 3.0 mg/ml.

10. The method of claim 9, wherein the matrix is seeded with about $5\times10^5$ to about $2\times10^6$ ECFCs/ml.

11. The method of claim 9, wherein the ECFCs cultured in a matrix seeded with about $2\times10^6$ ECFCs/ml have an increased vacuole density and vacuole area relative to ECFCs cultured in a matrix seeded with about $5\times10^5$ ECFCs/ml.

12. The method of claim 8, wherein the polymerized matrix of Type I acid soluble collagen has a ratio of collagen oligomers to collagen monomers of 50:50.

13. The method of claim 8, further comprising implanting the population of endothelial colony forming cells (ECFCs) embedded in the polymerized Type I acid soluble collagen matrix into a diseased area of a patient.

14. The method of claim 13, wherein the diseased area of the patient comprises an ischemic limb.

* * * * *

SEQUENCE LISTING

<160> NUMBER OF SEQ ID NOS: 8

<210> SEQ ID NO 1
<211> LENGTH: 24
<212> TYPE: DNA
<213> ORGANISM: Artificial Sequence
<220> FEATURE:
<223> OTHER INFORMATION: forward primer for ATP5B

<400> SEQUENCE: 1
ccactaccaa gaagggatct atca                                              24

<210> SEQ ID NO 2
<211> LENGTH: 19
<212> TYPE: DNA
<213> ORGANISM: Artificial Sequence
<220> FEATURE:
<223> OTHER INFORMATION: reverse primer for ATP5B

<400> SEQUENCE: 2
gggcagggtc agtcaagtc                                                    19

<210> SEQ ID NO 3
<211> LENGTH: 23
<212> TYPE: DNA
<213> ORGANISM: Artificial Sequence
<220> FEATURE:
<223> OTHER INFORMATION: primer for Cdc42

```
<400> SEQUENCE: 3
catcggaata tgtaccgact gtt                                    23

<210> SEQ ID NO 4
<211> LENGTH: 25
<212> TYPE: DNA
<213> ORGANISM: Artificial Sequence
<220> FEATURE:
<223> OTHER INFORMATION: reverse primer for Cdc42

<400> SEQUENCE: 4
tgcagtatca aaagtccaa gagta                                   25

<210> SEQ ID NO 5
<211> LENGTH: 22
<212> TYPE: DNA
<213> ORGANISM: Artificial Sequence
<220> FEATURE:
<223> OTHER INFORMATION: primer for MT1-MMP

<400> SEQUENCE: 5
ctgtcaggaa tgaggatctg aa                                     22

<210> SEQ ID NO 6
<211> LENGTH: 19
<212> TYPE: DNA
<213> ORGANISM: Artificial Sequence
<220> FEATURE:
<223> OTHER INFORMATION: reverse primer for MT1-MMP

<400> SEQUENCE: 6
aggggtcact ggaatgctc                                         19

<210> SEQ ID NO 7
<211> LENGTH: 23
<212> TYPE: DNA
<213> ORGANISM: Artificial Sequence
<220> FEATURE:
<223> OTHER INFORMATION: primer for Rac1

<400> SEQUENCE: 7
ctgatcagtt acacaaccaa tgc                                    23

<210> SEQ ID NO 8
<211> LENGTH: 24
<212> TYPE: DNA
<213> ORGANISM: Artificial Sequence
<220> FEATURE:
<223> OTHER INFORMATION: reverse primer for Rac1

<400> SEQUENCE: 8
cattggcaga ataattgtca aaga                                   24
```